(12) United States Patent
Ben-Yehuda et al.

(10) Patent No.: US 7,517,949 B2
(45) Date of Patent: Apr. 14, 2009

(54) LIVIN-DERIVED PEPTIDES, COMPOSITIONS AND USES THEREOF

(75) Inventors: Dina Ben-Yehuda, Mevasseret Zion (IL); Yaqoub Ashhab, Hebron (IL); Boaz Nachmias, Ramat-Gan (IL)

(73) Assignee: Hadasit Medical Research Services & Development Ltd., Jerusalem (IL)

( * ) Notice: Subject to any disclaimer, the term of this patent is extended or adjusted under 35 U.S.C. 154(b) by 0 days.

(21) Appl. No.: 10/559,639

(22) PCT Filed: May 31, 2004

(86) PCT No.: PCT/IL2004/000461

§ 371 (c)(1),
(2), (4) Date: Jul. 24, 2006

(87) PCT Pub. No.: WO2004/106371

PCT Pub. Date: Dec. 9, 2004

(65) Prior Publication Data

US 2007/0244040 A1 Oct. 18, 2007

(30) Foreign Application Priority Data

Jun. 2, 2003 (IL) .................................... 156263

(51) Int. Cl.
*C07K 14/47* (2006.01)
*A61K 38/00* (2006.01)
*C12P 21/06* (2006.01)
*C12N 15/00* (2006.01)
*C07H 21/04* (2006.01)

(52) U.S. Cl. .................... 530/300; 435/69.1; 435/320.1; 536/23.1; 536/23.5

(58) Field of Classification Search ....................... None
See application file for complete search history.

(56) References Cited

U.S. PATENT DOCUMENTS 5,108,921 A 4/1992 Low et al.
5,444,150 A 8/1995 Inman et al.

FOREIGN PATENT DOCUMENTS

WO WO 00/08144 2/2000

OTHER PUBLICATIONS

Kasof et al., Livin, a novel inhibitor of apoptosis protein family member. J Biol. Chem., 276, 3238-3246, 2001.*
Crnkovic-Mertens et al. Isoform-specific silencing of the Livin gene by RNA interference defines Livin β as key mediator of apoptosis inhibition in HeLa cells. J Mol. Med. 84, 232-240, 2006.*
Nachmias et al., Caspase-Mediated Cleavage Converts Livin from an Anti apoptotic to a Pro apoptotic Factor: Implications for Drug-Resistant Melanoma. Cancer Res. 63, 6340-6349, 2003.*
Yaqqub Ashhab et al., Two splicing variants of a new inhibitor of apoptosis gene with different biological properties and tissue distribution pattern, FEBS Letters, 2001, vol. 495, pp. 56-60.
Xuetao Cao et al., Lympotactin Gene-Modified Bone Marrow Dendritic Cells ACT as More Potent Adjuvants for Peptide Delivery to Induce Specific Antitumor Immunity, The Journal of Immunology, 1998, vol. 161, pp. 6238-6244.
Jijie Chai et al., Structural Basis of Caspase-7 Inhibition by XIAP, Cell Mar. 9, 2001, vol. 104, pp. 769-780.
Crozet Y. et al., Synthesis and characterization of cyclic pseudopeptide libraries containing thiomethylene and thiomethylenesulfoxide amide bond surrogates, Mol Divers, 1997-1998, vol. 3, No. 4, pp. 261-276.
Rene Daniel et al., Retroviral Transfer of Antisense Sequences Results in Reduction of C-Abl and Induction of Apoptosis in Hemopoietic Cells, Journal of Biomedical Science, 1998, vol. 5, pp. 383-394.
Quinn L. Deveraux et al., Cleavage of human inhibitor of apoptosis protein XIAP results in fragments with distinct specificities for caspases, The EMBO Journal, 1999, vol. 18, No. 19, pp. 5242-5251.
Aimee L. Edinger et al., Use of GPR1, GPR15, and STRL33 as Coreceptors by Diverse Human Immunodeficiency Virus Type 1 and Simian Immunodeficiency Virus Envelope Proteins, Virology, 1998, vol. 249, pp. 367-378.
Michael F. Giblin et al., Design and characterization of Alpha-Melanotropin peptide analogs cyclized through rhenium and technetium metal coordination, Proc. Natl. Acad. Sci. USA, Oct. 1998, vol. 95, pp. 12814-12818.
Griscelli F. et al., Heart-specific targeting of beta-galactosidase by the ventricle-specific cardiac myosin light chain 2 promoter using adenovirus vectors, Hum. Gene Ther., Sep. 1, 1998, vol. 9, No. 13, pp. 1919-1928.
M. Guang-Lin et al., Adenovirus-Mediated Gene Transfer of CTLA4IG Gene Results in Prolonged Survival of Heart Allograft, Transplantation Proceedings, 1998, vol. 30, pp. 2923-2924.
Guerra PI et al., PEGylation prevents the N-terminal degradation of megakaryocyte growth and development, Pharmaceutical Research, Dec. 1998, vol. 15, No. 12, pp. 1822-1827.
Ramesh Hedge et al., Identification of Omi/HtrA2 as a Mitochondrial Apoptotic Serine Protease That Disrupts Inhibitor of Apoptosis Protein-Caspase Interaction, The Journal of Biological Chemistry, Jan. 4, 2002, vol. 277, No. 1, pp. 432-438.

(Continued)

*Primary Examiner*—Elly-Gerald Stoica
(74) *Attorney, Agent, or Firm*—Martin Fleit; Paul D. Bianco; Fleit Gibbons Gutman Bongini & Bianco PL

(57) ABSTRACT

The present invention relates to livin-derived peptides with pro-apoptotic activity. More specifically, the present invention provides peptides p30-Livin α and p28-Livin β, derived from Livin α and β, respectively, as well as compositions thereof. These herein described peptides display pro-apoptotic activity. Thus, another object of the present invention is the use of the peptides or compositions thereof for the enhancement and/or induction of apoptosis, as well as for the treatment of cancer. Finally, the invention also provides a method of enhancing the sensitivity of cells to death-inducing treatments or agents through the use of the peptides of the invention.

10 Claims, 8 Drawing Sheets

OTHER PUBLICATIONS

Hemmi S. et al., The presence of human coxsackievirus and adenovirus receptor is associated with efficient adenovirusmediated transgene expression in human melanoma, Human Gene Therapy, Nov. 1, 1998, vol. 9, No. 16, pp. 2363-2373.

Yihua Huang et al., Structural Basis of Caspase Inhibition by XIAP: Differential Roles of the Linker versus the BIR Domain, Cell, Mar. 9, 2001, vol. 104, pp. 781-790.

Hideyuki Ikeda et al., Characterization of an Antigen That is Recognized on a Melanoma Showing Partial HLA Loss by CTL Expressing an NK Inhibitory Receptor, Immunity, Feb. 1997, vol. 6, pp. 199-208.

Veronika Jesenberger et al., Deadly Encounter: Ubiquitin Meets Apoptosis, Nature Reviews Molecular Cell Biology, Feb. 2002, vol. 3, pp. 112-121.

Gary M. Kasof et al., Livin, a Novel Inhibitor of Apoptosis Protein Family Member, The Journal of Biological Chemistry, Feb. 2, 2001, vol. 276, No. 5, pp. 3238-3246.

Eric C. Lacasse et al., The Inhibitors of apoptosis (IAPs) and their emerging role in cancer, Oncogene, 1998, vol. 17, pp. 3247-3259.

Lehmann F. et al., Differences in the antigens recognized by cytolytic T cells on two successive metastases of a melanoma patient are consistent with immune selection, European Journal of Immunology, Feb. 1995, vol. 25, No. 2, pp. 340-347.

Limal D. et al., Solid-phase synthesis and on-resin cyclization of a disulfide bong peptide and lactam analogues corresponding to the major antigenic site of HIV gp41 protein, The Journal of Peptide Research, Aug. 1998, vol. 52, No. 2, pp. 121-129.

Jiing-Huey Lin et al., KIAP, a Novel Member of the Inhibitor of Apoptosis Protein Family, Biochemical and Biophysical Research Communications, Nov. 22, 2000, vol. 279, pp. 820-831.

Loo DT et al., Measurement of cell death, Methods in Cell Biology, 1998, vol. 57, pp. 251-264.

M. Lotem et al., Autologous cell vaccine as a post operative adjuvant treatment for high-risk melanoma patients (AJCC stages III and IV), British Journal of Cancer, 2002, vol. 86, pp. 1534-4539.

Ofer Mandelboim et al., Protection from Lysis by Natural Killer Cells of Group 1 and 2 Specificity Is Mediated by Residue 80 in Human Histocompatibility Leukocyte Antigen C Alleles and Also Occuers with Empty Major Histocompatibility Complex Molecules, J. Exp. Med., Sep. 1996, vol. 184, pp. 913-922.

Mark P. Mattson, Apoptosis in Neurodegenerative Disorders, Nature Revies Molecular Cell Biology, Oct. 2000, vol. 1, pp. 120-129.

Shozo Muranishi et al., Lipophilic Peptides: Synthesis of Lauroyl Thyrotropin-Releasing Hormone and Its Biological Activity, Pharmaceutical Research, 1991, vol. 8, No. 5, pp. 649-652.

Ko Narumi et al., Adenovirus Vector-Mediated Perforin Expression Driven by a Glucocorticoid-Inducible Promoter Inhibits Tumor Growth In Vivo, American Journal of Respiratory Cell and Molecular Biology, 1998, vol. 19, pp. 936-941.

Nishida K. et al., Adenovirus-mediated gene transfer to nucleus pulposus cells. Implications for the treatment of intervertebral disc degenetation, Spine, Nov. 15, 1998, vol. 23, No. 22, pp. 2437-2442.

Panzone G. et al., A novel glycopeptide carrying a 3-oxazolin-5-one ring obtained by intra-molecular cyclization, J. Antibiot., Sep. 1998, vol. 51, No. 9, pp. 872-879.

Patel G. et al., A cyclic peptide analogue of the loop III region of platelet-derived growth factor-BB is a synthetic antigen for the native protein, J. Pept. Res., Jan. 1999, vol. 53, No. 1, pp. 68-74.

Lee C. Pederson et al., Combied Cytosine Deaminase Expression, 5-Fluorocytosine Exposure, and Radiotherapy Increases Cytotoxicity to Cholangiocarcinoma Cells, Journal of gastrointestinal Surgery, 1998, vol. 2, pp. 283-291.

Angel Porgador et al., Natural killer cell lines kill autologous beta2-microglobulin-deficient melanoma cells: Implications for cancer immunotherapy, Proc. Natl. Acad. Sci. USA, Nov. 1997, vol. 94, pp. 13140-13145.

Jeffrey C. Rathmell et al., Pathways of Apoptosis in Lymphocyte Development, Homeostasis, and Disease, Cell, Apr. 2002, vol. 109, pp. S98-S107.

Reed CJ, Apoptosis and cancer: strategies for integrating programmed cell death, Seminars in Hematology, vol. 37, 4 Suppl. 7, pp. 9-16, 2000.

Reissmann S. et al., Design, synthesis and characterization of bradykinin antagonists via cyclization of the modified backbone, Biomedical Pept. Proteins Nucleic Acids, 1994-1995, vol. 1, pp. 51-56.

Stefan J. Riedl et al., Structural Basis for the Inhibition of Caspase-3 by XIAP, Cell, Mar. 9, 2001, vol. 104, pp. 791-800.

Jean Rivier et al., Astressin Analogues (Corticotropin-Releasing Factor Antagonists) with Extended Duration of Action in the Rat, Journal of Medicinal Chemistry, 1998, vol. 41, No. 25, pp. 5012-5019.

Romanovskis P. et al., Preparation of head-to-tail cyclic peptides via sidechain attachment: implications for library synthesis, J. Pept. Res., Nov. 1998, vol. 52, No. 5, pp. 356-374.

Guy S. Salvesen et al., IAP Proteins: Blocking the Road to Death's Door, Nature Reviews Molecular Cell Biology, Jun. 2002, vol. 3, pp. 401-410.

Paul Schwarzenberger et al., IL-17 Stimulates Granulopoiesis in Mice: Use of an Alternate, Novel Gene Therapy-Derived Method for In Vivo Evaluation of Cytokines, The Journal of Immunology, 1998, vol. 161, pp. 6383-6389.

Sommary Soukchareun et al., Use of Nalpha-Fmoc-cysteine (S-thiobutyl) Derivatized Oligodeoxynucleotides for the Preparation of Oligodeoxynucleotide—Peptide Hybrid Molecules, Bioconjugate Chem., 1998, vol. 9, pp. 466-475.

Henning R. Stennicke et al., Internally quenched fluorescent peptide substrates disclose the subsite preferences of human caspases 1,3,6,7 and 8, Biochemical J., 2000, vol. 350, pp. 563-568.

Yasuyuki Suzuki et al., X-linked Inhibitor of Apoptosis Protein (XIAP) Inhibits Caspase-3 and -7 Distinct Modes, The Journal of Biological Chemistry, Jul. 20, 2001, vol. 276, No. 29, pp. 27058-27063.

Ryosuke Takahashi et al., A Single BIR Domain of XIAP Sufficient for Inhibiting Caspases, The Journal of Biological Chemistry, Apr. 3, 1998, vol. 273, No. 14, pp. 7787-7790.

Gerrard Teoh et al., Adenovirus Vector- Based Purging of Multiple Myeloma Cells, Blood, Dec. 15, 1998, vol. 92, No. 12, pp. 4591-4601.

Nancy A. Thornberry et al., A Combinatorial Approach Defines Specificities of Members of the Caspase Family and Granzyme B, The Journal of Biological Chemistry, Jul. 18, 1997, vol. 272, No. 29, pp. 17907-17911.

Valero ML et al., A comparative study of cyclization strategies applied to the synthesis of head-to-tail cyclic analogs of a viral epitope, J. Pept. Res., Jan. 1999, vol. 53, No. 1, pp. 56-67.

Domagoj Vucic et al., ML-IAP, a novel inhibitor of apoptosis that is preferentially expressed in human melanomas, Current Biology, 2000, vol. 10, pp. 1359-1366.

Domagoj Vucic et al., SMAC Negatively Regulates the Anti-apoptotic Activity of Melanoma Inhibitor of Apoptosis (ML-IAP), The Journal of Biological Chemistry, Apr. 5, 2002, vol. 277, pp. 12275-12279.

Susan Wang et al., Folate-mediated targeting of antineoplastic drugs, imaging agents, and nucleic acids to cancer cells, Journal of Controlled Release, 1998, vol. 53, pp. 39-48.

Janice White et al., Soluble Class I MHC with Beta2-Microglobulin Covalently Linked Peptides: Specific Binding to a T Cell Hybridoma, The Journal of Immunology, 1999, vol. 162, pp. 2671-2676.

Yili Yang et al., Ubiquitin Protein Ligase Activity of IAPs and Their Degradation in Proteasomes in Response to Apoptotic Stimuli, Science, May 5, 2000, vol. 288, pp. 874-877.

Chongxi Yu et al., Synthesis and Study of Peptides with Semirigid i and i + 7 Side-chain Brigdes Designed for Alpha-Helix Stabilization, Bioorganic & Medical Chemistry, 1999, vol. 7, pp. 161-175.

Zacharia S. et al., New reduced peptide bond substance P agonists and antagonists: effects on smooth muscle contraction, Eur. J. Pharmacol., Oct. 22, 1991, vol. 203, No. 3, pp. 353-357.

Shengle Zhang et al., Selection of Tumor Antigens as Targets for Immune Attack Using Immunohistochemistry: Protein Antigens, Clinical Cancer Research, Nov. 1998, vol. 4, pp. 2669-2676.

Database EMBL BIR7 sequence (Feb. 28, 2003) XP002296040 Database accession No. Q96CA5.

M. Germana Sanna et al., IAP Suppression of Apoptosis Involves Distinct Mechanisms: the TAK1/JNK1 Signaling Cascade and Caspase Inhibition, Molecular and cellular Biology, Mar. 2002, vol. 22, No. 6, pp. 1754-1766.

* cited by examiner

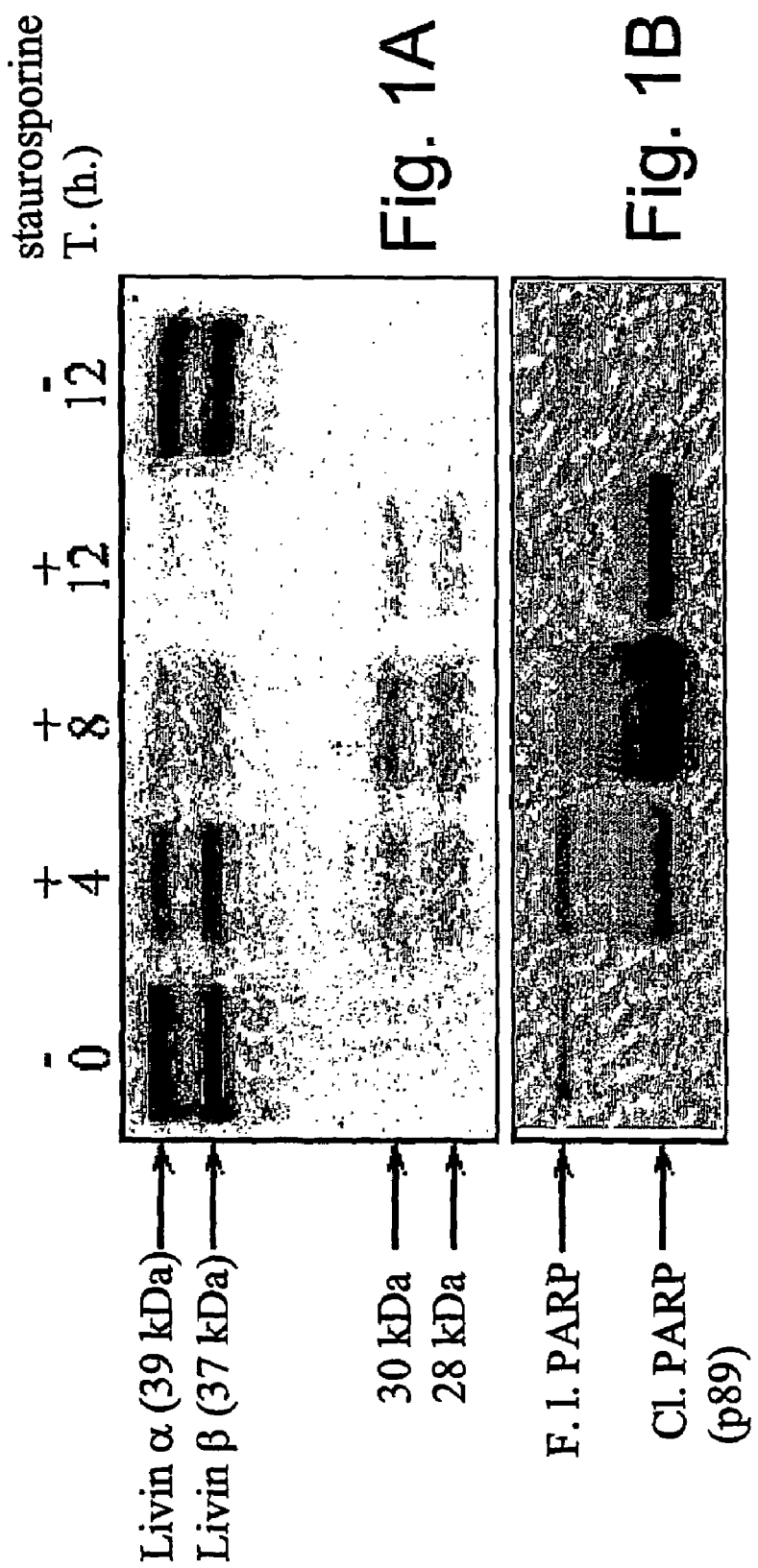

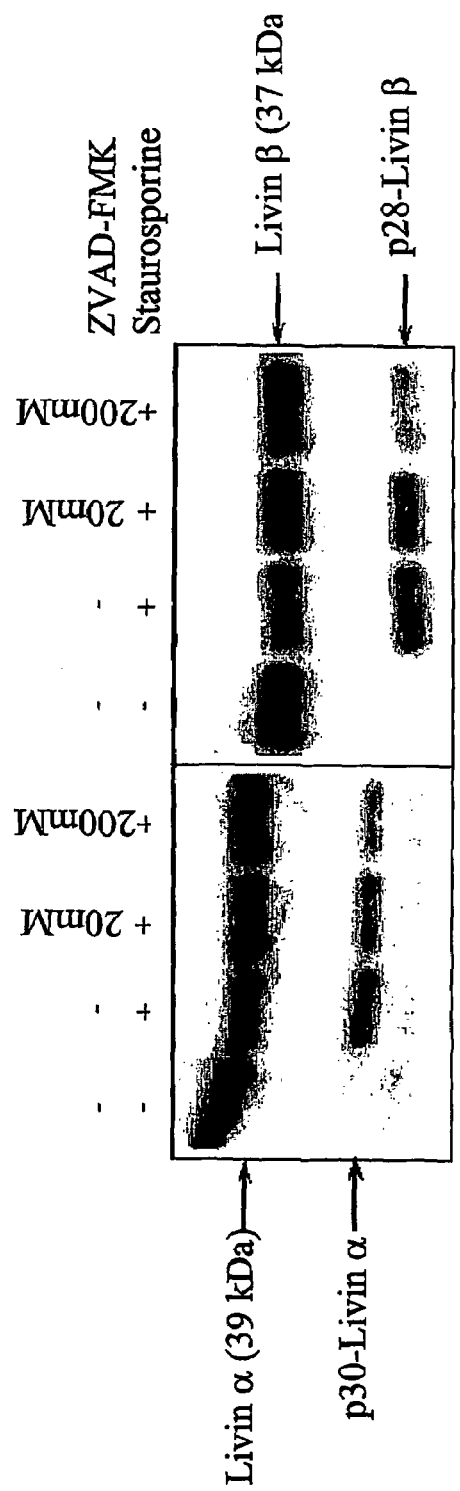
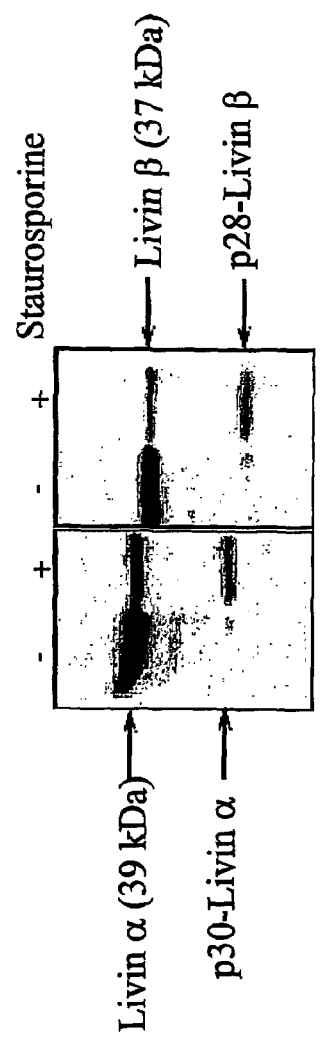
Fig. 3A
Fig. 3B

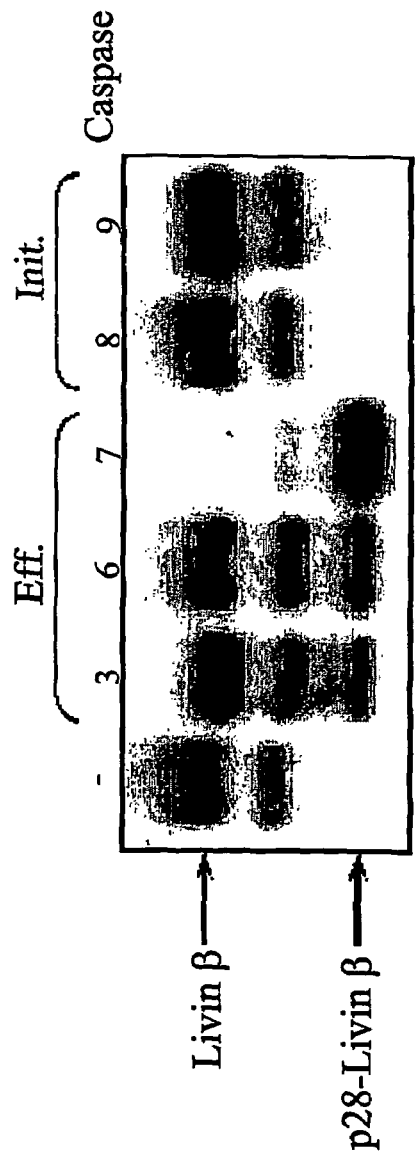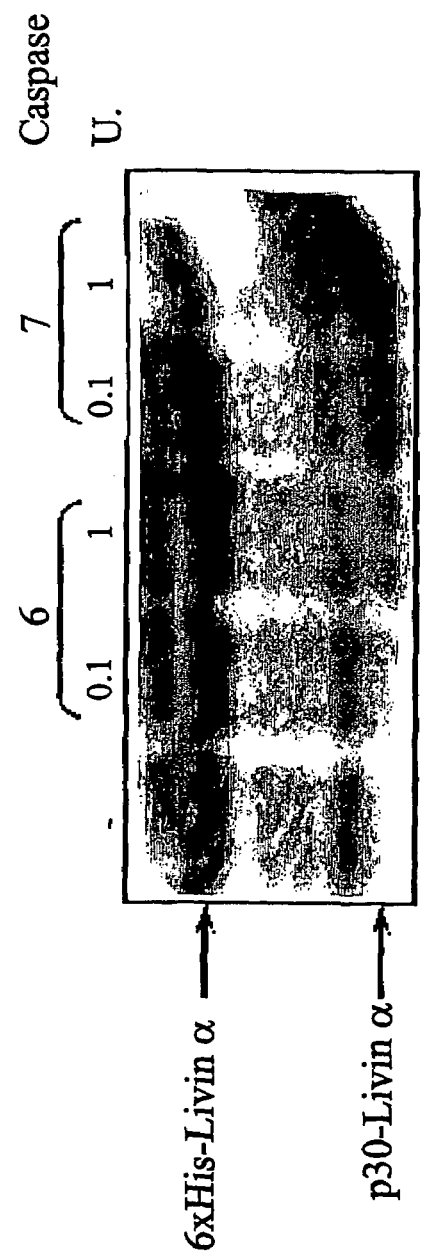
Fig. 4A
Fig. 4B

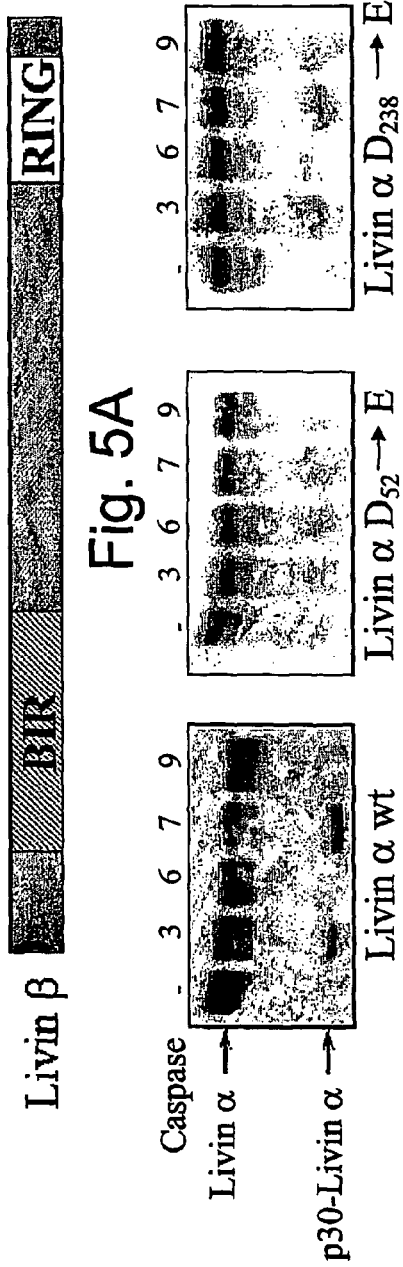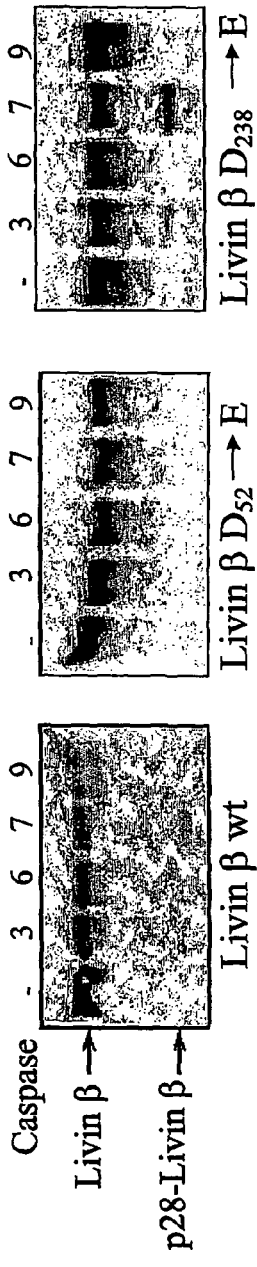
Fig. 5A
Fig. 5B

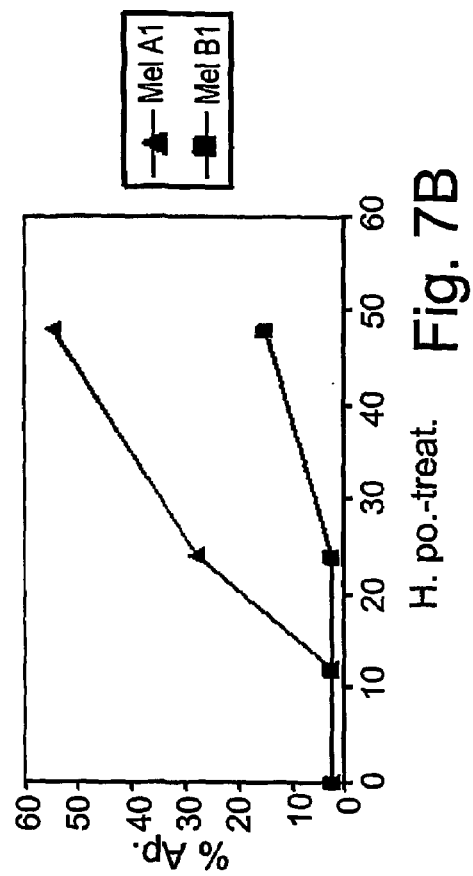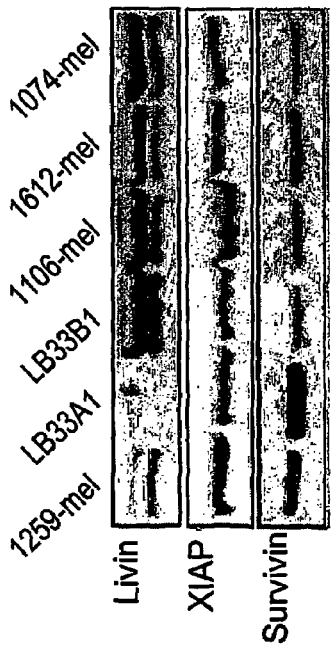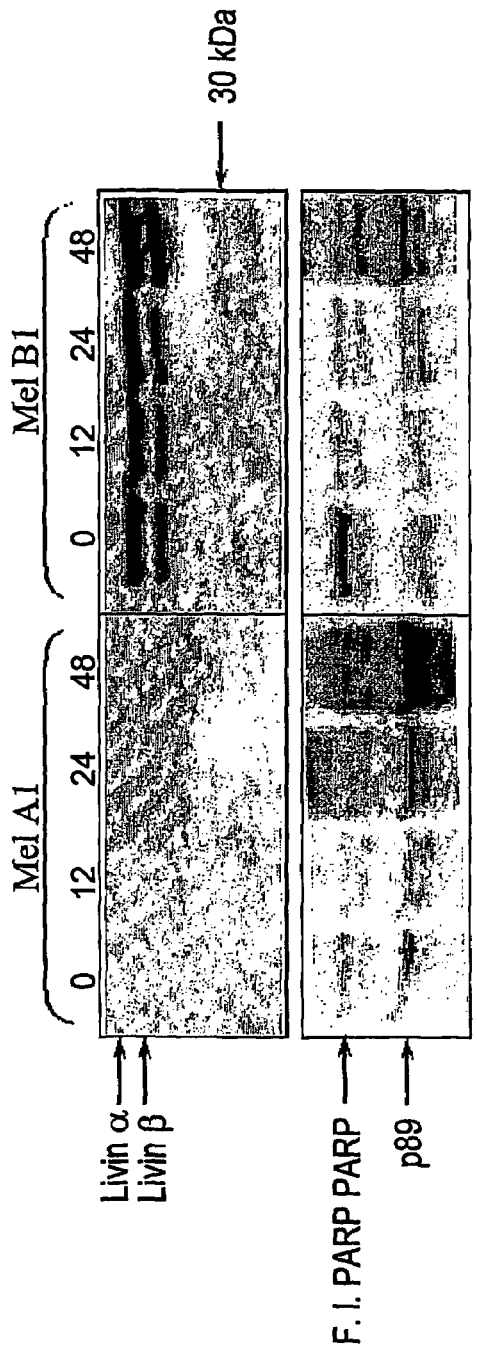
Fig. 7A
Fig. 7B
Fig. 7C

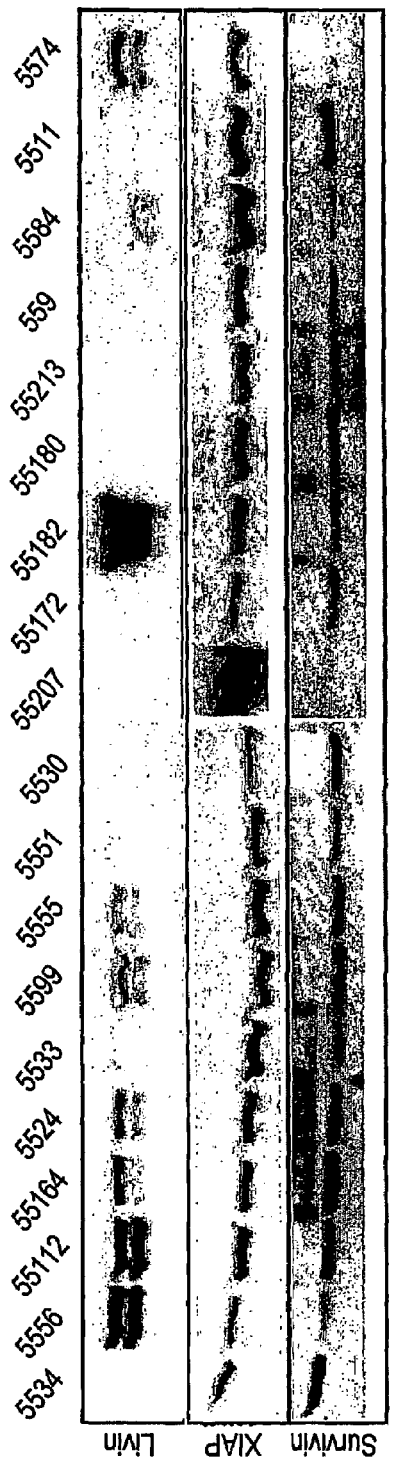
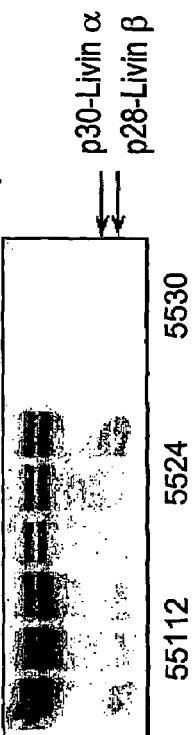
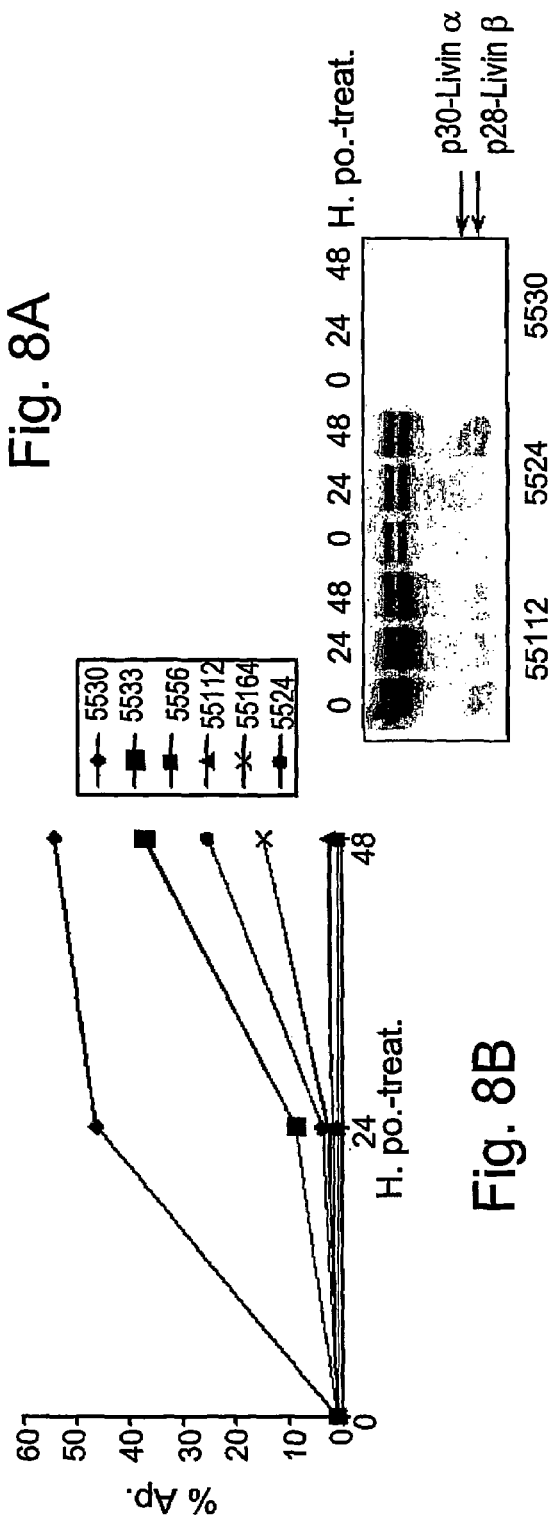
Fig. 8A
Fig. 8B
Fig. 8C

LIVIN-DERIVED PEPTIDES, COMPOSITIONS AND USES THEREOF

FIELD OF THE INVENTION

The present invention relates to the field of programmed cell death. More specifically, the present invention refers to peptides that display pro-apoptotic properties.

BACKGROUND OF THE INVENTION

All publications mentioned throughout this application are fully incorporated herein by reference, including all references cited therein.

Apoptosis is an active mechanism of cell death controlling the development and homeostasis of multicellular organisms. Tight regulation is required to ensure a delicate balance of life and death. Indeed, loss of apoptosis regulation results in a wide variety of diseases. Excess apoptosis might result in neurodegenerative disorders [Mattson, M. P. (2000) *Nat. Rev. Mol. Cell Biol.*, 1: 120-129], reperfusion injury after ischemic episodes [Rathmell, J. C. and Thompson, C. B. (2002) *Cell*, 109 Suppl: S97-107], and immunodeficiency [Reed, C. J. (2000) *Semin. Hematol.*, 37: 9-16]. On the other hand, lack of apoptosis is involved in cancer [LaCasse, E. C. et al. (1998) *Oncogene*, 17: 3247-3269], and autoimmune disorders [Rathmell, J. C. and Thompson, C. B. (2002) *id ibid*]. Several gene families are involved in the negative regulation of apoptosis, including the Inhibitor of Apoptosis Proteins (IAP). The products of the IAP gene family, discovered during the last five years, play a key role in apoptosis regulation and have become increasingly prominent in the field of cancer [Salvesen, G. S. and Duckett, C. S. (2002) *Nat. Rev. Mol. Cell Biol.*, 3:401-410]. So far, eight human IAPs have been identified: c-IAP1, c-IAP2, NAIP, Survivin, XIAP, Bruce, ILP-2, and Livin. These proteins contain one or more repeats of a highly conserved 70 amino acids domain termed the baculovirus IAP repeat (BIR), located at the amino-terminal. With the exception of NIAP and Survivin, human IAPs contain a conserved sequence termed RING finger at the carboxy-terminal. IAPs can block apoptosis mainly through their ability to bind and inhibit specific caspases [Stennicke, H. R. et al. (2000) *Biochem. J.*, 350 Pt 2: 563-568]. Initially, the molecular interaction between IAPs and caspases was thought to be mediated through the BIR domain [Takahashi, R. et al. (1998) *J. Biol. Chem.*, 273: 7787-7790]. However, recent crystallographic resolution studies revealed that conserved amino acids in the linker region between BIR1 and BIR2 of XIAP are the most critical for its interaction with caspases 3 and 7. Surprisingly, the BIR2 domain itself has almost no direct contact with caspases 3 and 7 [Chai, J. et al. (2001) *Cell*, 104: 769-780; Huang, Y. et al. (2001) *Cell*, 104: 781-790; Riedl, S. J. et al. (2001) *Cell*, 104: 791-800]. The linker region preceding BIR2 can inhibit caspases through its ability to sterically hinder the substrate access. Yet, this region alone is not sufficient, and the BIR domain is required to either align or stabilize the structure. The BIR domain has also a regulatory function, as molecules such as SMAC/Diablo and HtrA2, that inhibit IAPs function, bind to this region [Hegde, R. (2002) *J. Biol. Chem.*, 277: 432-438]. Several reports showed that many proteins containing a RING domain have E3-ubiquitin ligase activity. This activity is important in mediating the transfer of ubiquitin both to heterologous substrates as well as to the protein itself, thus targeting them to intracellular degradation [Suzuki, Y. et al. (2001) *J. Biol. Chem.*, 276: 27058-27063; Yang, Y. et al. (2000) *Science*, 288: 874-877]. Indeed, several IAPs were shown to mediate RING-dependent ubiquitylation of caspases as well as to themselves [Jesenberger, V. (2002) *Nat. Rev. Mol. Cell Biol.*, 3: 112-121]. Yet, the full potential of this function in apoptosis regulation remains unclear.

The essential role that IAPs play in the apoptotic process suggests that their activity must be tightly regulated. Indeed, it was reported that IAPs are regulated at the transcriptional/posttranscriptional levels as well as by interaction with inhibitory proteins [Vucic, D. et al. (2002) *J. Biol. Chem.*, 277: 12275-12279]. Another important mechanism to negatively regulate IAPs is the ability of certain caspases, such as caspases 3 and 7 to specifically cleave these anti-apoptotic proteins [Ikeda, H. et al. (1997) *Immunity*, 6: 199-208].

Among the IAP family, XIAP and cIAP1 were shown to undergo a site-specific cleavage that is mediated by caspases [Deveraux, Q. L. et al. (1999) *Embo J.*, 18: 5242-5251].

The present inventors and other groups have reported a novel IAP member, which was designated Livin/ML-IAP/KIAP [Vucic, D. et al. (2000) *Curr. Biol.*, 10: 1359-1366; Lin, J. H. et al. (2000) *Biochem. Biophys. Res. Commun.*, 279: 820-831; Kasof, G. M. (2001) *J. Biol. Chem.*, 276: 3238-3246; Ashhab, Y. et al. (2001) *FEBS Lett.*, 495: 56-60]. Livin contains a single BIR domain at the N-terminus and a carboxy-terminal RING domain. The inventors have previously demonstrated that Livin encodes two splicing variants, termed Livin α and β [Ashhab, Y. et al. (2001) *id ibid*]. These two proteins are highly similar, except for 18 amino acids located between the BIR and the RING domains, which are present in the α but not in the β isoform.

In the present invention, the inventors demonstrate that Livin undergoes site-specific cleavage by effector caspases 3 and 7, producing a large C-terminal subunit containing both the BIR and RING domains. Moreover, both Livin α and β undergo this cleavage, thus generating Livin-derived peptides α and β.

Unexpectedly, the inventors have found that the two Livin-derived peptides have pro-apoptotic properties. The present invention provides said pro-apoptotic peptides, together with compositions and uses thereof In addition, the present invention provides methods utilizing these Livin-derived peptides.

These and other objects of the present invention will become apparent as the description proceeds.

SUMMARY OF THE INVENTION

Little is known about the anti-apoptotic effect of Livin and virtually nothing is known about its regulatory mechanism. In the present invention, the inventors demonstrate that Livin undergoes site-specific cleavage by effector caspases 3 and 7, which results in a large C-terminal subunit containing both the BIR and RING domains. Interestingly, this subunit does not only lose its original anti-apoptotic function, but rather it acts, in a paradoxical fashion, as a pro-apoptotic factor that inflicts more cell death.

Thus, in a first aspect, the present invention provides a Livin-derived peptide. Said peptide is either p30-Livin α or p28-Livin β, as defined herein, wherein said p30-Livin α peptide comprises the sequence substantially as defined in SEQ. ID. NO.1, or functional analogues, derivatives or fragments thereof, and p28-Livin β peptide comprises the sequence substantially as defined in SEQ. ID. NO.2, or functional analogues, derivatives or fragments thereof The present invention relates, in a second aspect, to a pharmaceutical composition for inducing apoptosis, or programmed cell death, comprising as active ingredient a Livin-derived peptide. Preferably, said apoptosis is induced by a treatment or agent selected from any one of etoposide, anti-CD95/Fas, TNFα and staurosporine.

The present invention also refers to the use of the above-described pharmaceutical composition as an agent for enhancing the sensitivity of cells to death-inducing treatments or agents.

In another aspect, the present invention refers to the use of a Livin-derived peptide, as defined by the invention, for the induction of apoptosis or programmed cell death. Preferably, the peptide of the invention is to be used in the induction of programmed cell death of malignant cells.

In a further aspect, the present invention relates to the use of a Livin-derived peptide as an agent for enhancing the sensitivity of cells to death-inducing treatments or agents, wherein said peptide comprises a sequence as defined in any one of SEQ. ID. NO.1 or SEQ. ID. NO.2. Preferably, said death-inducing treatments or agents are selected from any one of etoposide, anti-CD95/Fas, TNFα and staurosporine.

In a yet further aspect, the invention provides a method for the preparation of a pharmaceutical composition for the induction of apoptosis, wherein said method involves admixing any one of the peptides as defined by SEQ. ID. NO.1 or SEQ. ID. NO.2, with a pharmaceutically acceptable adjuvant, carrier or diluent, and optionally with at least one additional active agent.

In an even further aspect, the present invention provides a method of enhancing the sensitivity of cells to death-inducing treatments or agents, wherein said method comprises the steps of:
(a) Introducing a Livin-derived peptide comprising a sequence essentially as defined in any one of SEQ. ID. NO.1 or SEQ. ID. NO.2 into a cell; and
(b) Treating said cell with death-inducing agents or treatments.

Finally, the present invention refers to the use of the pharmaceutical composition as defined by the invention for the treatment of cancerous cells.

The invention will be further described on the hand of the following figures, which are illustrative only and do not limit the scope of the invention which is defined by the appended claims.

BRIEF DESCRIPTION OF THE FIGURES

FIG. 1a-b: Cleavage of Endogenous Livin During Staurosporine-Induced Apoptosis.

MeWo cells were plated 24 h. prior to staurosporine (1 μM) exposure. At the indicated times cells were lysed, normalized for total protein and analyzed by Western blot.

FIG. 1a: Western blot using monoclonal anti-Livin antibody that detects both full length Livin as well as the cleavage products;

FIG. 1b: Western blot using anti-PARP antibody. The ratio between full-length PARP and its cleavage fragment (p89) serves as a marker of apoptosis. PARP cleavage fragment (p89) was detected more strongly than full length PARP, probably due to a higher affinity of the antibody.

(+) or (−) refer to the presence or absence of staurosporine treatment.

Abbreviations: T., time; F.l., full length; Cl. Cleaved.

FIG. 2a-d: Livin Cleavage is a Ubiquitous Phenomenon.

Figures 2A, 2B, 2C, 2D:
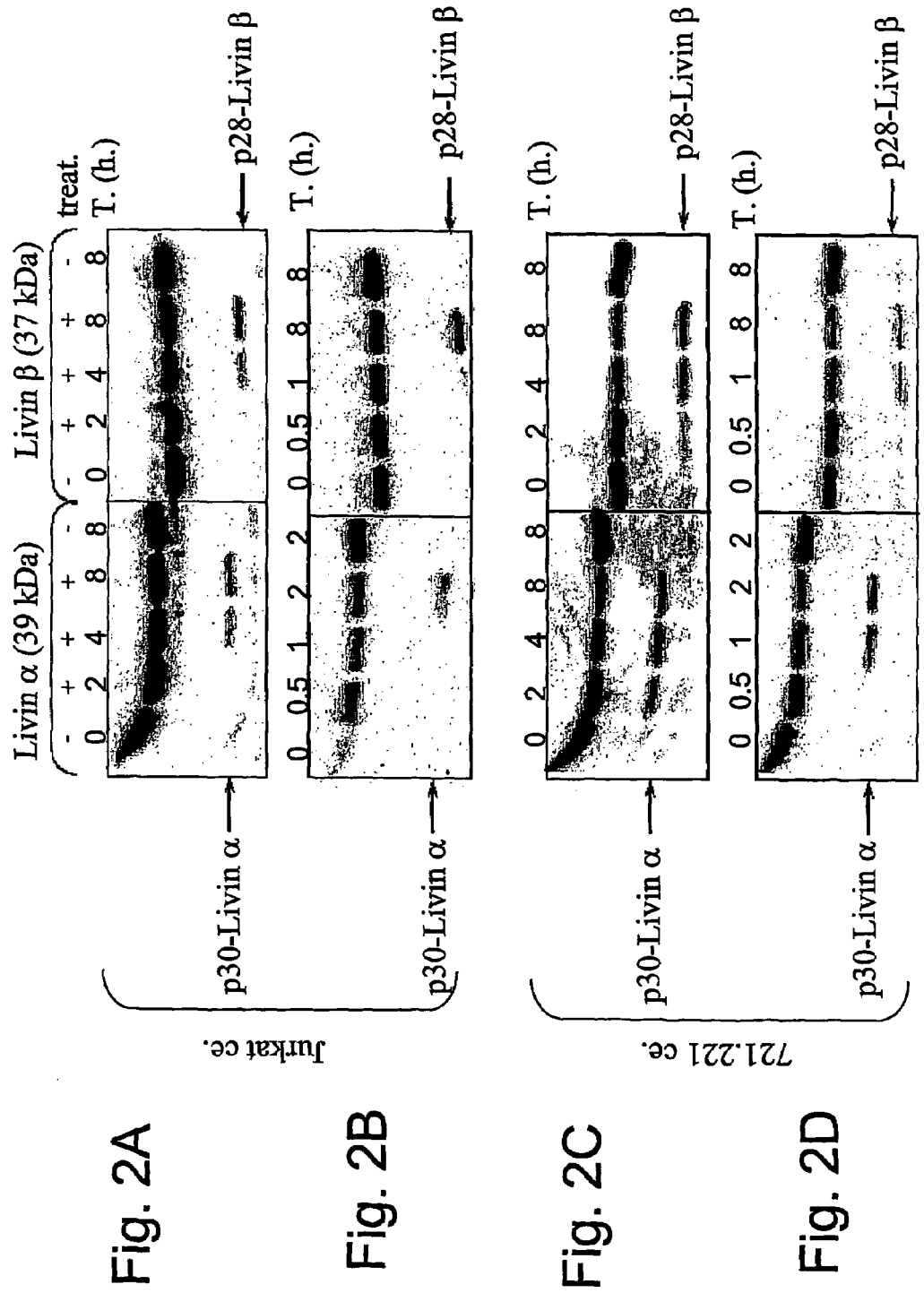

Livin α or β were stably transfected into different cell lines, and treated with various apoptotic stimuli. Livin cleavage was detected in:

FIG. 2a: Jurkat T-cell leukemia/Lymphoma cells treated with etoposide 2.5 μg/ml.

FIG. 2b: Jurkat T-cell leukemia/Lymphoma cells treated with staurosporine 0.5 μM.

FIG. 2c: 721.221 EBV-transformed B cell line treated with etoposide 5 μg/ml.

FIG. 2d: 721.221 EBV-transformed B cell line treated with staurosporine 0.5 μM.

Abbreviations: ce, cells; treat., treatment; T., time.

FIG. 3a-b: Livin cleavage is caspase-mediated.

FIG. 3a: Jurkat cells transfected with either Livin α or β were incubated for 1 hour in the presence or absence of 20 mM or 200 mM ZVAD-FMK, a pan-caspase inhibitor, prior to treatment with staurosporine (0.5 μM) to induce apoptosis.

FIG. 3b: MCF-7, a breast cancer cell line null for caspase 3, was stably transfected with Livin α or β and treated with staurosporine (2 μM) for 12 hours to induce apoptosis. Livin was detected using anti-Livin antibody.

FIG. 4a-b: Effector but not initiator caspases cleave Livin in vitro.

6×His-Livin α and β were generated in bacteria and purified on a nickel column.

FIG. 4a: Recombinant Livin β was incubated for 30 minutes at 37° C. with: either no caspase (−), caspase 3 (60U), caspase 6 (3U), caspase 7 (0.75 U), caspase 8 (90U) or caspase 9 (2U). The units (U) for caspases 3 and 8 are defined differently than for caspases 6, 7 and 9. Using an appropriate colorimetric substrate, similar activity was achieved with caspases 3 and 7.

FIG. 4b: Recombinant Livin α was incubated with either no caspase (−), or caspases 6 and 7, at the indicated amounts. The samples were then resolved on gel and analyzed using anti-Livin antibody (Ab). Unspecific bands that resulted from the purification were also detected.

Abbreviations: Eff., effector; Init., initiator.

FIG. 5a-b: Livin is cleaved at aspartic acid 52.

FIG. 5a: Schematic of the full-length Livin α and β, showing the BIR and RING domains, and the 18 amino acids difference between the two isoforms (black box). The mutation sites D52 and D238 are marked by arrows.

FIG. 5b: cDNAs encoding full-length Livin α and β, or the mutant forms Livin D52E and D238E were translated in vitro in reticulocyte lysate. The products of the translation reactions were incubated for 30 min. with caspase 3 (60U), caspase 6 (2U), caspase 7 (1U), and caspase 9 (1U). Reactions were then resolved on gel and analyzed with anti-Livin antibodies.

FIG. 6a-d: Cleavage of Livin eliminates its anti-apoptotic effect and produces a pro-apoptotic subunit.

Figure 6A:
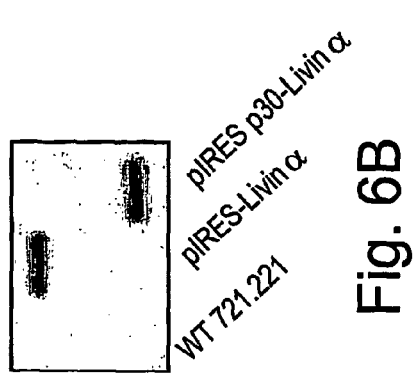

FIG. 6a: 721.221 cells stably expressing either Livin α or p30 Livin β, and wild type 721.221 cells, were treated with 0.1 μg/ml anti-CD95/Fas antibody for 18 hours. Nuclear morphology was visualized using acridine orange staining and used for determining apoptosis rate. Apoptotic cells were scored when the nuclei displayed chromatin condensation and/or nuclear fragmentation.

Figure 6B:
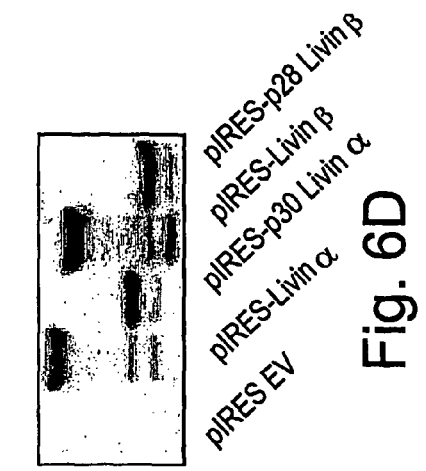

FIG. 6b: Western blot analysis confirming the expression of the appropriate proteins.

Figure 6C:
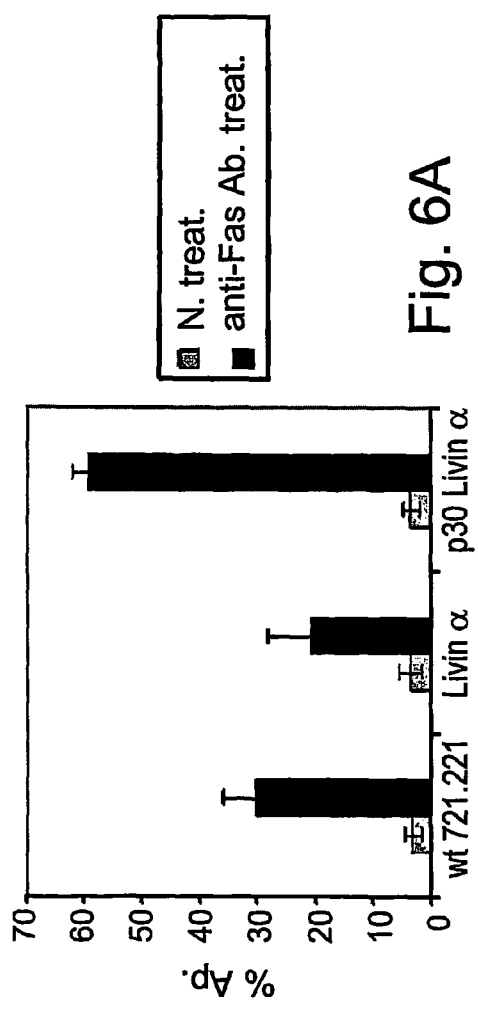

FIG. 6c: 293T cells were transiently transfected with the indicated plasmids. 24 hours post-transfection, cells were harvested and analyzed by flow cytometry. Apoptosis of GFP-positive cells was analyzed by Annexin-V/PI stain.

Figure 6D:
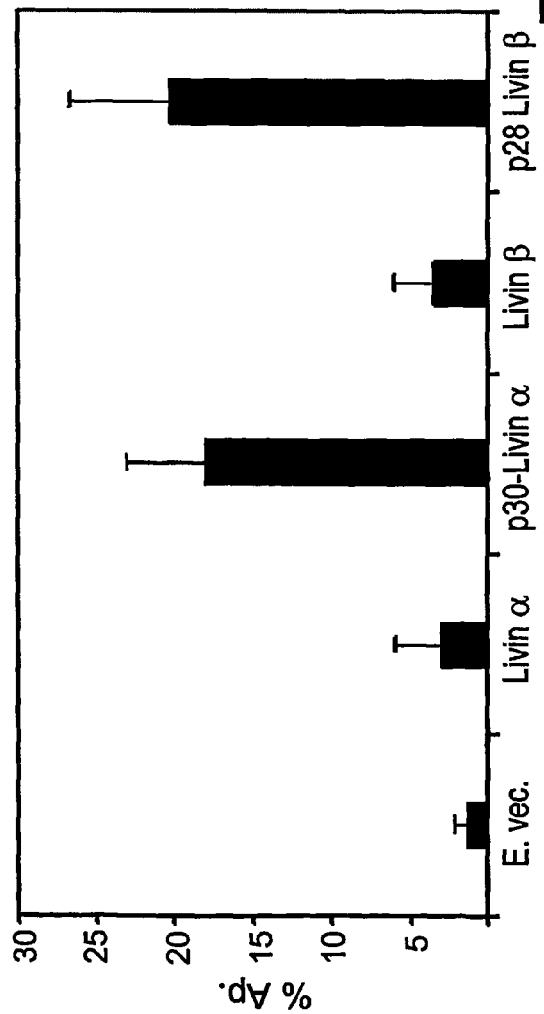

FIG. 6d: Western blot analysis of transiently transfected 293T cells 24 hours post-transfection, showing the expression of the appropriate proteins.

Abbreviations: Ap., apoptosis; N. treat, no treatment; treat., treatment; E. vec., empty vector; Ab., antibody.

FIG. 7a-c: Post-vaccination metastatic melanoma cell line over-expresses Livin, rendering the cells resistant to chemotherapy.

(a) Melanoma cell lines were lysed, normalized for total protein and analyzed for Livin, XIAP and Survivin expression.

(b) Melanoma cell lines LB33 Mel A1 and B1 were treated with etoposide (15 µg/ml). Apoptosis rate was determined by nuclear morphology, as described.

(c) Western blot analysis of the Melanoma cell line LB33 Mel A1 and B1 for Livin (upper panel) and PARP cleavage as a marker of apoptosis (lower panel)

Abbreviations: Ap., apoptosis; H. po.-treat., hours post-treatment; F.l., full-length.

FIG. 8a-c: Livin expression in primary melanoma cells mediates etoposide resistance.

FIG. 8a: Livin, XIAP and Survivin expression was determined in 19 primary cultures of melanoma cells derived from patient's tumors (numbers indicate patient's code).

FIG. 8b: Six samples were selected according to the level of Livin expression (high: 5556, 55112, moderate: 5524, 55164, or undetectable: 5530, 5533). These samples were treated with etoposide (20 µg/ml). Apoptosis rate was determined by nuclear morphology, as described. The data shown are representative of three independent experiments, which were also confirmed by flow cytometry, using sub-G1 assay.

FIG. 8c: Three samples that represent the different levels of Livin expression were lysed and Western blot analysis was performed using anti-Livin antibody.

Abbreviations: Ap., apoptosis; H. po.-treat., hours post-treatment.

DETAILED DESCRIPTION OF THE INVENTION

The following terms used throughout this specification are defined herein:

p30-Livin α: Livin α-derived peptide, cleavage product, which may also be synthetically produced, having the following amino acid sequence (SEQ. ID. NO.1)
GQILGQLRPLTEEEEEEGAGATLSRGPAFPGMGSEELRLASFYDWPLTAE

VPPELLAAAGFFHTGHQDKVRCFFCYGGLQSWKRGDDPWTEHAKWFPSCQ

FLLRSKGRDFVHSVQETHSQLLGSWDPWEEPEDAAPVAPSVPASGYPELP

TPRREVQSESAQEPGGVSPAEAQRAWWVLEPPGARDVEAQLRRLQEERTC

KVCLDRAVSIVFVPCGHLVCAECAPGLQLCPICRAPVRSRVRTFLS p28-Livin β: Livin β-derived peptide, cleavage product, which may also be synthetically produced, having the following amino acid sequence (SEQ. ID. NO.2)
GQILGQLRPLTEEEEEEGAGATLSRGPAFPGMGSEELRLASFYDWPLTAE

VPPELLAAAGFFHTGHQDKVRCFFCYGGLQSWKRGDDPWTEHAKWFPSCQ

FLLRSKGRDFVHSVQETHSQLLGSWDPWEEPEDAAPVAPSVPASGYPELP

TPRREVQSESAQEPGARDVEAQLRRLQEERTCKVCLDRAVSIVFVPCGHL

VCAECAPGLQLCPICRAPVRSRVRTFLS

Apoptosis: is the process of programmed cell death, or cell suicide. It is a form of cell death distinct from necrosis. Programmed cell death is the regulated elimination of cells that occurs naturally during the course of development, as well as in many pathological circumstances. This deliberate elimination of cells occurs in a morphologically distinct manner that suggests an active, gene-directed process.

Livin, a new member of the LAP family, was recently described by the inventors and by other groups [Vucic, D., et al, (2000) id ibid; Ashhab Y., et al. (2001) id ibid]. Originally, it was shown that Livin has two isoforms, Livin α (SEQ. IID. NO.3) and Livin β (SEQ. ID. NO.4), with different anti-apoptotic properties and tissue distribution patterns [Ashhab Y., et al. (2001) id ibid].

In the present invention, the inventors demonstrate, for the first time, that following apoptotic stimuli, both Livin isoforms α and β undergo a specific proteolytic cleavage that trims the 52 amino acids at the N-terminus of Livin. From each isoform, a C-terminal Livin subunit is thus produced, of approximately 30 and 28 kDa, respectively, containing the full BIR and RING domains.

Thus, in a first aspect, the present invention provides a Livin-derived peptide. Said peptide is either p30-Livin α or p28-Livin β, as defined herein, wherein said p30-Livin α peptide comprises the sequence substantially as defined in SEQ. ID. NO.1, or functional analogues, derivatives or fragments thereof, and p28-Livin β peptide comprises the sequence substantially as defined in SEQ. ID. NO.2, or functional analogues, derivatives or fragments thereof.

As shown in Example 1 and FIG. 1a-b, Livin cleavage appeared early after the apoptotic stimuli and before significant levels of apoptosis were detected, suggesting Livin cleavage is an early key regulator that controls the progression of apoptosis.

The peptides of the invention may be isolated or synthetic.

By "analogs and derivatives" is meant the "fragments", "variants", "analogs" or "derivatives" of said Livin-derived peptide molecule. A "fragment" of a molecule is meant to refer to any peptide subset of the molecule. A "variant" of such molecule is meant to refer a naturally occurring molecule substantially similar to either the entire molecule or a fragment thereof. An "analog" of a molecule can be without limitation a paralogous or orthologous molecule, e.g. a homologous molecule from the same species or from different species, respectively.

Derivatives of the peptides of the invention may be the result of the addition of amino acid sequences or domains to the peptide of the invention. It may be desired to separate such additional sequences from the Livin-derived part of the sequence by way of a linker sequence. Linker sequences may consist mainly of amino acids that do not provide spatial constraints, such as Glycine and preferably Alanine. An example for a flexible peptide linker sequence is described in e.g., [White et al. (1999) J. Immunol. 162, 2671-6].

The peptide of the invention comprises most preferably SEQ. ID. NO. 1 or 2. However, it is to be understood that the invention pertains to any peptide comprising sequence structurally similar to Livin sequence with substantially equal or greater pro-apoptotic activity. Changes in the structure of the peptide comprise one or more deletions, additions, or substitutions. The number of deletions or additions, which may occur at any point in the sequence, including within the Livin-derived sequence, will generally be less than 25%, preferably less than 10% of the total amino acid number.

Preferred substitutions are changes that would not be expected to alter the secondary structure of the peptide, i.e., conservative changes. The following list shows amino acids that may be exchanged (left side) for the original amino acids (right side).

| Original Residue | Exemplary Substitution |
| --- | --- |
| Ala | Gly; Ser |
| Arg | Lys |
| Asn | Gln; His |
| Asp | Glu |
| Cys | Ser |
| Gln | Asn |
| Glu | Asp |
| Gly | Ala; Pro |
| His | Asn; Gln |
| Ile | Leu; Val |
| Leu | Ile; Val |
| Lys | Arg; Gln; Glu |
| Met | Leu; Tyr; Ile |
| Phe | Met; Leu; Tyr |
| Ser | Thr |
| Thr | Ser |
| Trp | Tyr |
| Tyr | Trp; Phe |
| Val | Ile; Leu |

Amino acids can also be grouped according to their essential features, such as charge, size of the side chain, and the like. The following list shows groups of similar amino acids. Preferred substitutions would exchange an amino acid present in one group with an amino acid from the same group.

1. Small aliphatic, non-polar: Ala, Ser, Thr Pro, Gly;
2. Polar negatively charged residues and their amides: Asp, Asn, Glu, Gln;
3. Polar positively charged residues: His, Arg, Lys;
4. Large aliphatic non-polar residues: Met, Leu, Ile, Val, Cys;
5. Large aromatic residues: Phe, Tyr, Trp.

Further comments on amino acid substitutions and protein structure may be found in additional references [Schulz et al. (1987) *Principles of Protein Structure*, Springer-Verlag, New York, N.Y.; Creighton, T. E. (1983) *Proteins: Structure and Molecular Properties*, W.H. Freeman & Co., San Francisco].

The preferred conservative amino acid substitutions as detailed above are expected to substantially maintain or increase the function or activity of the peptide of the invention, as detailed herein below. Of course, any amino acid substitutions, additions, or deletions are considered to be within the scope of the invention where the resulting peptide is a peptide of the invention, i.e., a peptide which is substantially equal or superior in terms of function to the preferred peptide of the invention. Similarly, fragments, analogues or derivatives which display similar activity as the peptides of the invention are also part of the claimed invention.

The peptide of the invention may be further modified to improve its function, affinity, or stability. For instance, cyclization may be used to impart greater stability and/or overall improved performance upon the peptide. A number of different cyclization methods have been developed, including side chain cyclization and backbone cyclization. These methods are well documented in the prior art [Yu et al. (1999) *Bioorg. Med. Chem.* 7, 161-75; Patel et al. (1999) *J. Pept. Res.* 53, 68-74; Valero et al. (1999) *J. Pept. Res.* 53, 56-67; Romanovskis et al. (1998) *J. Pept. Res.* 52, 356-74; Crozet et al. (1998) *Mol. Divers.* 3, 261-76; Rivier et al. (1998) *J. Med. Chem.* 41, 5012-9; Panzone et al. (1998) *J. Antibiot. (Tokyo)* 51, 872-9; Giblin et al. (1998) *Proc. Natl. Acad. Sci. USA* 95, 12814-8; Limal et al., (1998) *J. Pept. Res.* 52:121-9; U.S. Pat. No. 5,444,150]

A preferred method of cyclization involves stabilization of an amphipathic alpha-helix by using para-substituted amino acid derivatives of a benzene ring [Yu et al. (1999) *id ibid.*]. Another preferred method of cyclization is backbone cyclization [Reissmann et al. (1994-95) *Biomed. Pept. Proteins Nucleic Acids* 1:51-6, and references therein]. A relatively new method of cyclization which involves backbone-to side chain connections may also be used [Reissmann et al. (1994-95) *id ibid.*].

Other modifications as known in the art may be carried out. For instance, it may be desirable to link polyethylenglycol (PEG) groups to the peptide. Such groups may impart enhanced stability upon the peptide. Another effect of these groups may be lowered immunogenicity. This feature of PEG-linked these groups may be lowered immunogenicity. This feature of PEG-linked peptides may be particularly desirable when the peptide of the invention is to be used in vivo. Preparation of PEG-linked peptides has been described [Guerra et al. (1998) *Pharm. Res.* 15:1822-7].

The present invention provides Livin-derived peptides. A therapeutic or research-associated use of these tools may necessitate their introduction into or interaction with tissue cultured cells or cells of a living organism. For this purpose, it is desired to improve membrane permeability of the peptides. The principle of derivatization with lipophilic structures may be used in creating peptides with enhanced membrane permeability. For instance, the sequence of a known membranotropic peptide may be added to the sequence of the peptide of the invention [Soukchareun et al. (1998) *Bioconjug. Chem.* 9, 466-75]. Further, the peptide may be derivatized by partly lipophilic structures such as Palmityl or Geraniol groups. For instance, lauroyl derivatives of peptides have been described by Muranishi et al., Pharm. Research 8, 649, 1991. Further modifications of peptides comprise the oxidation of methionine residues to thereby create sulfoxide groups [Zacharia et al. (1991) *Eur. J. Pharmacol.* 203, p. 353]. Zacharia and coworkers also describe peptide or derivatives wherein the relatively hydrophobic peptide bond is replaced by its ketomethylene isoester ($COCH_2$). These and other modifications known to the person of skill in the art of protein and peptide chemistry enhance membrane permeability.

Another way of enhancing membrane permeability is the use of receptors, such as virus receptors, on cell surfaces in order to induce cellular uptake of the peptide or protein. This mechanism is used frequently by viruses, which bind specifically to certain cell surface molecules. Upon binding, the cell takes the virus up into its interior. The cell surface molecule is called a virus receptor. For instance, the integrin molecules CAR and AdV have been described as virus receptors for Adenovirus [Hemmi et al. (1998) *Hum. Gene Ther.* 9, 2363-73] and references therein. The CD4, GPR1, GPR15, and STIRL33 molecules have been identified as receptors/co-receptors for HIV [Edinger et al. (1998) *Virology* 249, 367-78].

Thus, conjugating the peptides to molecules that are known to bind to cell surface receptors will enhance membrane permeability of said peptides. Examples for suitable groups for forming conjugates are sugars, vitamins, hormones, cytokines, transferrin, asialoglycoprotein, and the like molecules. Low et al. [U.S. Pat. No. 5,108,921] describe the use of these molecules for the purpose of enhancing membrane permeability of peptides, and the preparation of said conjugates. Of course, as one type of the cells targeted by the peptide of the invention are melanoma cells, it is advantageous to chose a cell surface protein that will occur preferably on such cells, such as a melanoma cell surface marker.

The above use of cell surface proteins for enhancing membrane permeability of a peptide of the invention may also be used in targeting said peptide of the invention to certain cell types or tissues. For instance, if it is desired to target cancer cells, it is preferable to use a cell surface protein that is expressed more abundantly on the surface of those cells. Examples are the folate receptor, the mucin antigens MUC1, MUC2, MUC3, MUC4, MUC5AC, MUC5B, and MUC7, the glycoprotein antigens KSA, carcinoembryonic antigen, prostate-specific membrane antigen (PSMA), HER-2/neu, and human chorionic gonadotropinbeta. Wang et al. (1998) teaches the use of folate to target cancer cells [Wang and Low (1998) *J. Control Release* 53(1-3), 39-48] and Zhang et al. (1998) teaches the relative abundance of each of the other antigens noted above in various types of cancer and in normal cells [Zhang et al. (1998) *Clin. Cancer Res.* 4, 2669-76]. As the peptide of the invention preferably acts to promote apoptosis, other markers may be used, as advantageous in each particular case.

The peptide of the invention may therefore, using the above-described conjugation techniques, be targeted to certain cell type as desired. For instance, if it is desired to enhance apoptosis in cells of the lymphocytic lineage, a peptide of the invention may be targeted at such cells, for instance, by using the MHC class II molecules that are expressed on these cells. This may be achieved by coupling an antibody, or the antigen-binding site thereof, directed against the constant region of said MHC class II molecule to the protein or peptide of the invention. Further, numerous cell surface receptors for various cytokines and other cell communication molecules have been described, and many of these molecules are expressed in more or less tissue- or cell-type restricted fashion. Thus, for instance, when it is desired to target a subgroup of T cells, the CD4 T cell surface molecule may be used for producing the conjugate of the invention. CD4-binding molecules are provided by the HIV virus, whose surface antigen gp42 is capable of specifically binding to the CD4 molecule.

The peptides of the invention may be introduced into cells by the use of a viral vector. The use of vaccinia vector for this purpose is detailed in Chapter 16 of the above-noted Current Protocols in Molecular Biology. The use of Adenovirus vectors has been described [Teoh et al. (1998) *Blood* 92, 4591-4601; Narumi et al. (1998) *Am. J. Respir.* 19, 936-941; Pederson et al. (1998) *J. Gastrointest. Surg.* 2, 283-91; Guang-Lin et al. (1998) *Transplant. Proc.* 30, 2923-4; Nishida et al. (1998) *Spine* 23, 2437-42; Schwarzenberger et al. (1998) *J. Immunol.* 161, 6383-9; Cao et al. (1998) *J. Immunol.* 161, 6238-44]. Retroviral transfer of antisense sequences has been described [Daniel et al. (1998) *J. Biomed. Sci.* 5, 383-94].

When using viruses as vectors, the viral surface proteins are generally used to target the virus. As many viruses, such as the above Adenovirus, are rather unspecific in their cellular tropism, it may be desirable to impart further specificity by using a cell-type or tissue-specific promoter. Griscelli et al. (1998) teach the use of the ventricle-specific cardiac myosin light chain 2 promoter for heart-specific targeting of a gene whose transfer is mediated by Adenovirus [Griscelli et al. (1998) *Hum. Gene Ther.* 9, 1919-28].

Thus, the present invention provides a Livin-derived, pro-apoptotic peptide. This peptide may be the cleavage product of Livin α, which is herein designated p30-Livin α. Alternatively, the peptide is the cleavage product of Livin β, which is herein designated p28-Livin β.

In a second aspect the present invention relates to a pharmaceutical composition for inducing apoptosis, or programmed cell death, comprising as active ingredient a Livin-derived peptide, wherein said Livin-derived peptide comprises the sequence substantially as defined in any one of SEQ. ID. NO.1 or SEQ. ID. NO.2, or functional analogues, derivatives or fragments thereof. Preferably, said apoptosis is induced by a treatment or agent selected from any one of etoposide, anti-CD95/Fas, TNFα, staurosporin. Preferably, the composition of the invention is for inducing programmed cell death in malignant cells.

The pharmaceutical composition of the invention may further comprise buffers, diluents and/or excipients. In particular, the pharmaceutical composition of the invention may further comprise protease inhibitors. Examples of protease inhibitors are PMSF, commercially available cocktails of protease inhibitors, etc.

The preparation of pharmaceutical compositions is well known in the art and has been described in many articles and textbooks, see e.g., Gennaro A. R. ed. (1990) *Remington's Pharmaceutical Sciences*, Mack Publishing Company, Easton, Pa., and especially pages 1521-1712 therein.

In another aspect, the present invention refers to the use of a Livin-derived peptide, as defined by the invention, for the induction of apoptosis or programmed cell death. Preferably, the peptide of the invention is to be used in the induction of programmed cell death of malignant cells.

The terms apoptosis and programmed cell death are used herein interchangeably.

In contrast to other IAP family members like XIAP and cIAP1, the present invention shows the first example of an IAP cleavage product that acts as a pro-apoptotic factor despite bearing a BIR domain. A possible explanation for this unique behavior is that an additional, as yet undetermined, motif at the first 52 amino acids of Livin can modulate the anti-apoptotic effect of the BIR domain. The absence of this motif might enhance the E3-ubiquitin ligase activity of the RING domain that in turn targets other anti-apoptotic proteins to proteasome-mediated degradation. The subunit might also act as a pseudo-substrate, hindering the activity of other IAP family members. These possibilities are currently being explored.

In a further aspect, the present invention relates to the use of the Livin-derived peptide of the invention as an agent for enhancing the sensitivity of cells to death-inducing treatments or agents. Preferably, said death-inducing treatments or agents are selected from any one of etoposide, anti-CD95/Fas TNFα and staurosporin, which are preferably used in malignant cells.

In a yet further aspect, the present invention refers to the use of the pharmaceutical composition of the invention as an agent for enhancing the sensitivity of cells to death-inducing treatments or agents.

In an even further aspect, the invention provides a method for the preparation of a pharmaceutical composition for the induction of apoptosis, wherein said method involves admixing any one of the peptides as defined by the invention with a pharmaceutically acceptable adjuvant, carrier or diluent, and optionally with at least one additional active agent.

Alternatively, the present invention provides a method of enhancing the sensitivity of cells to death-inducing treatments or agents, wherein said method comprises the steps of:
(a) Introducing a Livin-derived peptide as defined by the invention into a cell; and
(b) Treating said cell with death-inducing agents or treatments.

Preferably, said cells to be treated by this method are malignant cells.

In the context of the present invention, malignant cells refer to cells that are malignant or otherwise derived from solid as well as non-solid tumors. Thus, malignant cells are cell derived from any one of a malignant proliferative disorder, a cancer, a tumor and a hyperplasia of a tissue or organ. If the tissue is a part of the lymphatic or immune systems, malignant cells may include non-solid tumors of circulating cells. Malignancies of other tissues or organs may produce solid tumors. In general, the peptides or the compositions thereof, as well as the methods of the present invention may be used in the treatment of non-solid and solid tumors, for example, carcinoma, melanoma, leukemia, and lymphoma.

Therefore, according to a preferred embodiment, the peptide of the invention or a composition comprising the same, can be used for the treatment or inhibition of non-solid cancers, e.g. hematopoietic malignancies such as all types of leukemia, e.g. acute lymphocytic leukemia (ALL), acute myelogenous leukemia (AML), chronic lymphocytic leukemia (CLL), chronic myelogenous leukemia (CML), myelodysplastic syndrome (MDS), mast cell leukemia, hairy cell leukemia, Hodgkin's disease, non-Hodgkin's lymphomas, Burkitt's lymphoma and multiple myeloma, as well as for the treatment or inhibition of solid tumors such as tumors in lip and oral cavity, pharynx, larynx, paranasal sinuses, major salivary glands, thyroid gland, esophagus, stomach, small intestine, colon, colorectum, anal canal, liver, gallbladder, extraliepatic bile ducts, ampulla of vater, exocrine pancreas, lung, pleural mesothelioma, bone, soft tissue sarcoma, carcinoma and malignant melanoma of the skin, breast, vulva, vagina, cervix uteri, corpus uteri, ovary, fallopian tube, gestational trophoblastic tumors, penis, prostate, testis, kidney, renal pelvis, ureter, urinary bladder, urethra, carcinoma of the eyelid, carcinoma of the conjunctiva, malignant melanoma of the conjunctiva, malignant melanoma of the uvea, retinoblastoma, carcinoma of the lacrimal gland, sarcoma of the orbit, brain, spinal cord, vascular system, hemangiosarcoma and Kaposi's sarcoma.

In the present invention the inventors demonstrate the important role of the endogenous Livin in chemoresistance of melanoma cells. Primary cultures of melanoma cells were tested for the expression of Livin, XIAP and Survivin. XIAP and Survivin were widely expressed in most of the melanoma samples tested. On the other hand, Livin was expressed at variable levels, in 10 out of the 27 melanoma samples. Direct correlation between resistance to etoposide-induced apoptosis and Livin expression was observed in vitro. In contrast, expression of XIAP and Survivin did not correlate with drug-resistance. The ability of exogenously-expressed Livin β to inhibit etoposide-induced apoptosis was previously demonstrated by the inventors [Ashhab, Y. et al. (2001) id ibid]. Similar experiments showed the ability of exogenous Livin β to protect Jurkat cells against various other hemotherapeutic agents including Daunorubicin, Fludarabine and Cytosine arabinoside (unpublished data).

Interestingly, the clinical data relating to the patients from whom the cell lines used in Example 7 originated support the correlation found in vitro between chemotherapy resistance and Livin expression. Five out of the 7 patients who did not respond to chemotherapy had intermediate to high levels of Livin expression, whereas among the responding patients only 1 out of 8 expressed Livin and at a low level. Most importantly, these differences between chemotherapy responders and non-responders were found to be statistically significant.

The results shown in Example 7 strongly correlate Livin expression with chemotherapy resistance, i.e., with Livin having an anti-apoptotic effect. Hence, the pro-apoptotic effect of the Livin-derived peptides, which is the subject of the present invention, was a completely unexpected finding.

Consequently, the peptides of the present invention display great potential as agents for the induction of apoptosis, or programmed cell death, in target cells. Particularly, the peptides, as well as analogs and compositions comprised thereof may be used in the treatment of cancer. The introduction of peptides p30-Livin α or p28-Livin β, either alone or in combination, into cells is likely to direct them to the programmed cell death pathway. Alternatively, it might act to enhance the sensitivity of the cells to death-inducing agents or treatments. Appropriate cells for such treatment are cells derived from melanoma, lymphoma, T-cell leukemia, epithelial cells, human embryonic kidney cells (like the 293 HEK cell line) or the 721.221 cell line.

Hence, in a last aspect, the present invention refers to the use of the pharmaceutical composition as defined by the invention for the treatment of cancer.

In other words, the present invention provides a method of treatment of cancer, comprising administering a therapeutically effective amount of at least one Livin-derived peptide as defined in the invention, or compositions derived thereof, to a subject in need.

Various methods of administration may be used for delivering the peptides or pharmaceutical compositions derived thereof as defined by the invention to a subject in need. Peptides may be delivered via intravenous (i.v.), intramuscular (i.m.) intraperitoneal (i.p.) injections, orally (in liquid form or prepared as dosage unit forms like capsules, pills, lozenges, etc.). In order to be effective therapeutically, peptides should be prepared in a way that would enable their stability in the system following injection, or yet more preferably, following oral administration. Alternatively, the peptides of the invention may also be delivered via transdermal delivery using patches, ointment or cream. The medical professional in care of the subject in need shall determine the therapeutically effective dosage to be administered.

In summary, Livin is able to interfere with the apoptotic process immediately at the starting point. It can inhibit initiator caspase 9 [Kasof, G. M. and Gomes, B. C. (2001) *J Biol Chem*, 276: 3238-3246], but it cannot be cleaved by caspases 9 or 8. Once a sufficient apoptotic signal is received, the situation changes and effector caspases such as 3, 6 and 7, become activated and the cell is committed to apoptosis. Caspases 3 and 7 are also inhibited by Livin [Kasof, G. M. and Gomes, B. C. (2001) *id ibid*], but at the same time, as shown by the present inventors, they are able to cleave Livin, and convert it from an anti-apoptotic to a pro-apoptotic agent. Taken together, these results demonstrate the versatile nature of Livin in the apoptotic cascade.

In contrast to general peptidases, caspases cleave their targets at specific sites after aspartic acid. Therefore, caspase-mediated cleavage of several cellular proteins serves as a mechanism to produce subunits with modulated or new functions, rather than totally abolishing their effect. The presence of the intact BIR and RING domains in the C-terminal subunits of Livin for a relatively long time after the induction of apoptosis indicates an apoptosis-regulatory function of these subunits. Indeed, the experiments performed with 721.221 cells (Example 5, FIG. 6a-c) which stably expressed the cleaved subunit of Livin α, p30-Livin α, revealed that it not only loses its anti-apoptotic effect, but also gained significant pro-apoptotic activity. In spite of repeated attempts, the inventors were unable to generate 721.221 cells that stably expressed p28-Livin β. However, transient transfection experiments revealed that both Livin subunits have pro-apoptotic activity in 293T cells (Example 5 and 6, FIG. 6a-c). As shown in Example 6, the p28-Livin β subunit is a more potent pro-apoptotic agent than p30-Livin α (Example 6).

Disclosed and described, it is to be understood that this invention is not limited to the particular examples, process steps, and materials disclosed herein as such process steps and materials may vary somewhat. It is also to be understood that the terminology used herein is used for the purpose of describing particular embodiments only and not intended to be limiting since the scope of the present invention will be limited only by the appended claims and equivalents thereof.

It must be noted that, as used in this specification and the appended claims, the singular forms "a", "an" and "the" include plural referents unless the content clearly dictates otherwise.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The following examples are representative of techniques employed by the inventors in carrying out aspects of the present invention. It should be appreciated that while these techniques are exemplary of preferred embodiments for the practice of the invention, those of skill in the art, in light of the present disclosure, will recognize that numerous modifications can be made without departing from the spirit and intended scope of the invention.

EXAMPLES

Experimental Procedures

Cells and Apoptosis Induction

Jurkat human T cell leukemia/lymphoma cell line, and 721.221 EBV-transformed B cell line were grown in RPMI 1640. MCF-7 human breast carcinoma cells, 293T human embryonic kidney cells, and the melanoma cell lines LB33 Mel A1 and B1 (a generous gift from Coulie PG), 1259-mel, 1074-mel, 1106-mel and 1612-mel [Porgador, A. et al. (1997) Proc. Natl. Acad. Sci. USA, 94: 13140-13145] were grown in DMEM. Media were supplemented with 10% fetal calf serum, 100 U/ml penicillin, 100 µg/ml streptomycin, 1 mM L-glutamine.

Primary melanoma cells were derived and maintained as described [Lotem, M. et al. (2002) Br J Cancer, 86: 1534-1539].

To induce apoptosis, cells were treated with anti-CD95 antibody, clone DX2 (R&D Systems, MN, USA), staurosporine, a protein kinase C inhibitor, and the Topoisomerase II-inhibitor etoposide (Sigma, USA).

Western Blot Analysis and Antibodies

Whole cell lysates were prepared using lysis buffer (Tris-HCl 20 mM, EDTA 2 mM, β-2-Mercaptoethanol 6 mM, NP-40 1%, SDS 0.1%). Protease inhibitors included: PMSF 1 mM, Protease inhibitor cocktail (Sigma) diluted 1:10, and Complete inhibitor cocktail (Roche, Germany) diluted 1:25. About $0.25-1 \times 10^6$ cells were lysed in a total volume of 100 µl, incubated at 4° C. for 20 minutes with vigorous vortexing. Protein content was assessed by Bradford assay (Bio-Rad, Germany), according to the manufacturer's instructions. Samples were resolved on a 10% Bis-Tris pre-cast gel, following the manufacturer's instructions (Invitrogen, USA). After transferring the gel to a PVDF membrane (Millipore, Mass. USA), the membrane was exposed to the antibodies in blocking solution (PBS 1% Casein, 0.05% Tween 20) for 1 hour, followed by three 5-minute washes with PBS. The monoclonal antibody against Livin (clone:88C570) was purchased from Imgenex, and diluted 1:3000 in blocking solution. Survivin 6E4 monoclonal antibody was used according to the manufacturer's recommendation. For these antibodies, Envision-HRP (DAKO, Denmark) was used as a secondary antibody for Enhanced Chemiluminescence (ECL) reaction. Polyclonal antibodies against either PARP or XIAP (Cell Signaling, MA, USA) were diluted according to the manufacturer's recommendation. Anti-rabbit IgG HRP-linked antibody (Cell Signaling, MA, USA) was used as a secondary antibody. ECL reaction was performed by mixing solution A [6 ml Tris 100 mM pH=8.5, 3.3 µl H202 30%] with solution B [6 ml Tris 100 mM pH=8.5, 60 µl Luminol 250 mM (Sigma), 26.6 µl p-Coumeric acid 90 mM (Sigma)], for 1 minute in the dark.

Plasmid Constructs and Cell Transfection

The retroviral vector pLXSN (Clontech, Calif. USA) that contains the cDNA of either Livin α or β splicing variants were prepared as previously described (21). Cells were infected with the packaged particles, and were placed under selection using G418 (Sigma).

Transfection with the pIRES2-EGFP plasmid (QIAGEN, Germany) encoding p30-Livin α or p28-Livin β, and as positive controls, the full length wild type cDNA of either Livin α or β was done either by electroporation, in 721.221 cells [Mandelboim, O. et al. (1996) J. Exp. Med., 184: 913-922], or using PolyFect (QIAGEN), in human embryonic kidney 293T cells, according to manufacturers instructions. Since pIRES2-EGFP contains an internal ribosome entry site, it permits both the gene of interest and the EGFP gene to be translated from a single bicistronic mRNA. Thus, cells transfected with this plasmid may be monitored for transfection by the absence or presence of the GFP signal.

Site-directed Mutagenesis

Site-directed mutagenesis of pL-Livinα-SN or pL-Livinβ-SN was performed using a PCR-based megaprimer method [Brons-Poulsen, J. et al. (1998) Mol. Cell Probes, 12: 345-348]. The forward and the reverse flanking primers were the following: EcoRI-Start 5'-GGG GAATTCTGGTCAGAGCCAGTGTTC-3' (SEQ. ID. NO.5) and BamHI-Stop 5'-GGG GGATCCGGAGCCCACTCTGCA-3' (SEQ. ID. NO.6). The restriction sites used for subcloning are underlined. To generate a megaprimer that will introduce either the mutation D52E or D238E, the forward mutated primers D52E(F) 5'-CGTGGAaGGGCAGATCCT-3' (SEQ. ID. NO.7), and D238E(F) CCAGGGAaGTaGAGGCGCA (SEQ. ID. NO.8) were used respectively. Each of these forward primers was used with BamHI-Stop primer to generate the megaprimer with the mutated bases (lower case). In the primer D238E(F), an additional nonsense change was introduced at the third base of valine codon (GTa, as underlined above) in order to abolish the restriction site for BstXI, which will be used as a selection marker. The PCR product was purified with QIAquik column (QIAGEN). 300 ng of the purified megaprimer was then used as reverse primer with forward flanking primer EcoRI-Start.

To construct the cleavage fragment p30-Livin α and p28-Livin β, the forward primer EcoRI-start-53 5'-GGGGA-ATTCAGTGTTCCCTCCATGGGGCAGATCCTGGG-CCA-3' (SEQ. ID. NO. 9) (beginning of the translation in italics) was used with the primer BamHI-Stop. The Pwo DNA polymerase (Roche), which has proof-reading activity, was used for all cloning experiments. The PCR products were purified as above, then digested with the indicated restriction enzymes. The fragments were subcloned in the appropriate vector. In addition to using the absence of the restriction site for BstXI, as a selection marker, the introduction of the desired change was confirmed by sequencing each plasmid in both directions.

In vitro Transcription and Translation

The wild type cDNA of Livin α and β as well as the mutated cDNA $D_{52}$ to E or $D_{238}$ to E, were cloned in pCR2.1-plasimd (Invitrogen, USA). Plasmid DNA was in vitro transcribed and translated using the TNT T7 transcription-translation-coupled reticulocyte lysate system (Promega, USA). Each reaction contained 1 μg of plasmid DNA in a final volume of 50 μl. The reaction components and the conditions were according to the instructions of the manufacturer. The detection of the translated product was made by Western blot using anti-Livin antibody.

Production of 6xHis-recombinant Livin

For production of recombinant Livin, full-length cDNA of either α or β variants were cloned in frame with the N-terminally 6xHis-tag in the plasmid pQE30 (QIAGEN). The primers were Livin-Exp-F 5'-TGTTGGATCCATGG GACCTAAAGACA-3' (SEQ. ID. NO.10) and Livin-Exp-R 5'-GGCAAAGCTTCTAGGACAGGAAGGTGC-3' (SEQ. ID. NO.11), which have the underlined BamHI and HindIII restriction sites, respectively. The plasmids were introduced into *Escherichia coli* strain BL21(DE3). The 6xHis-tagged proteins were prepared from the soluble fraction upon induction with 1 mM isopropyl-1-thio-β-D-galactopyranoside at 37° C. for 3 h. The recombinant proteins were purified on a Nickel column (Pharmacia). Coomassie blue staining analysis following SDS-PAGE revealed >90% intact protein.

Apoptosis Assays

Nuclear morphology was visualized using acridin orange (Sigma) staining as described [Loo, D. T. et al. (1998) *Methods Cell Biol.*, 57: 251-264]. Apoptotic cells were scored when the nuclei displayed chromatin condensation and/or nuclear fragmentation. The percentage of apoptotic to viable cells was counted by fluorescence microscopy and 500 cells were scored for each sample. Flow cytometry analysis of the apoptotic cells was done using two different methods. In the Sub-G1 assay the cells were harvested, washed with PBS and fixed using 100% methanol. Following an overnight incubation at −20° C., cells were re-hydrated with PBS for 30 minutes on ice, and then resuspended in PBS with RNase A (50 μg/ml) and stained with Propidium Iodide (PI) (Sigma) at a final concentration of 5 μg/ml. Flow cytometry analysis was performed in FL2 histogram. Cells transfected with a GFP-containing plasmid were analyzed using Annexin-V-Cy5 and PI staining according to the manufacturer instructions (MBL, Japan). In stably transfected cultures with a rate of GFP-positive cells higher than 95%, all cells were analyzed for apoptosis. In transiently transfected cells, GFP expression was first analyzed (FL-1), and only GFP-positive cells were analyzed for Annexin-V-Cy5 (FL-4) and PI (FL-3) staining.

Caspase Inhibitors and In vitro Caspase Assay

Cells were incubated with caspase inhibitors for 1-2 hour prior to treatment with the apoptotic stimuli. Pan-caspase inhibitor Z-VAD-FMK (R&D systems, MN, USA), specific caspase 3 inhibitor Z-DQMD-FMK at 60 μM, and caspase 6 inhibitor VEID-CHO at 60 μM, were used (Calbiochem, Calif., USA). Recombinant caspases were purchased from Calbiochem and incubated for 30 minutes at 37° C. with recombinant Livin. According to the manufacturer, the units, of each recombinant caspase are defined differently. Units of caspases 3 and 8 are defined as the amount of enzyme that will release 1 pmol of pNA from either DEVD-pNA or Ac-IETD-pNA, respectively, per minute at 30° C. Units of caspases 6, 7 and 9 are defined as the amount of enzyme that will release 1 nmol of pNA from either, Ac-VEID-pNA, Ac-DEVD-pNA, or LEHD-pNA, respectively, per hour at 37° C. Caspase 3 and 7 activity was calibrated using a caspase activity assay (Calbiochem, Calif. USA). Caspase 9 activity was assessed using caspase-9 colorimetric substrate LEHD-pNA (Biovision, Calif., USA). Recombinant Granzyme B (Biomol, Pa., USA) activity was confirmed with Granzyme B activity assay kit (Biomol, Pa., USA), using Ac-IEPD-pNA.

General Methods of Molecular Biology

A number of methods of the molecular biology art are not detailed herein, as they are well known to the person of skill in the art. Such methods include PCR cloning, expression of cDNAs, analysis of recombinant proteins or peptides, transformation of bacterial and yeast cells, transfection of mammalian cells, and the like. Textbooks describing such methods are, e.g., Sambrook et al. (1989) *Molecular Cloning, A Laboratory Manual*, Cold Spring Harbor Laboratory, ISBN: 0879693096; F. M. Ausubel (1988) *Current Protocols in Molecular Biology*, ISBN: 047150338X, John Wiley & Sons, Inc. Furthermore, a number of immunological techniques are not in each instance described herein in detail, as they are well known to the person of skill in the art. See, e.g., Harlow and Lane (1988) *Antibodies: a laboratory manual*. Cold Spring Harbor Laboratory.

Example 1

Livin is Cleaved During the Apoptotic Process

Upon the induction of apoptosis in MeWo, a melanoma cell line that express high levels of Livin, specific cleavage of both Livin isoforms was observed. Full length Livin α and Livin β were detected as 39 and 37 kDa proteins (approximately), respectively. Treatment with staurosporine produced, in a time-dependent manner, detectable fragments of 30 kD and 28 kD, termed p30-Livin α and p28-Livin β, respectively (FIG. 1a). No cleavage was detected after 12 hours without treatment. This difference in molecular weight represents the difference between full length Livin a (39 kDa) and Livin β (37 kDa), and suggests a common cleavage site for both isoforms. Concomitantly with the appearance of the cleavage fragments, a marked depletion of the full length of both Livin isoforms was observed (FIG. 1a). The smaller fragment, of approximately 10 kDa, could not be detected due to the use of a monoclonal antibody that is specific to an epitope located on the large (and detectable) fragments.

PARP (poly ADP ribose polymerase) is a nuclear protein involved in DNA repair predominantly in response to environmental stress. This protein is one of the main targets of caspase 3. Cleavage of PARP facilitates cellular disassembly and serves as a marker of cells undergoing apoptosis. Following exposure to anti-Livin antibody, the membrane was striped and exposed to PARP antibody that detects full length PARP, as well as the large (89 kDa) and small (24 kDa) fragments. A clear correlation between the cleavage of Livin and the cleavage of PARP as a marker of caspase 3 activity and apoptosis was noted (FIG. 1b). A decrease in PARP was observed after 12 hours of treatment, probably due to protein degradation, as a consequence of a high rate of apoptosis.

To further explore the cleavage of each isoform, retroviral infection to establish a Jurkat T-cell Leukemia/Lymphoma cell line and an EBV-transformed B cell line 721.221, expressing high, stable levels of either Livin α or β were used. In their previous work, the inventors showed that both Livin isoforms can protect against anti-CD95/Fas antibody-induced apoptosis [Ashhab, Y. et al. (2001) id ibid]. Notably, testing other chemotherapeutic agents revealed different anti-apoptotic properties of Livin isoforms. While only Livin α can protect from staurosporine-induced apoptosis, Livin β can only block etoposide-induced apoptosis. A panel of the three drugs etoposide, staurosporine, and anti-CD95/Fas ligand was thus used to induce apoptosis in the transfected Jurkat and 721.221 cells. Consistently, both Livin isoforms were cleaved by etoposide-and staurosporine-induced apoptosis, as shown in FIG. 2a-d. Similar results were observed when cells were treated with anti-CD95/Fas antibody (data not shown). The correlation between the timing of the cleavage and apoptosis rate was further investigated. Notably, cleavage was observed as soon as 2 hours after the treatment with etoposide. However, Annexin-V staining revealed only minor levels of apoptosis (data not shown). This result suggested that Livin cleavage is an early event during the apoptotic process.

Example 2

Livin Cleavage is Caspase-Mediated

It was previously shown that a large group of proteins undergo specific cleavage by caspases during the apoptotic process. To determine whether Livin cleavage is also mediated by caspases, a pan caspase inhibitor zVAD-FMK was used. Pre-incubation of Jurkat cells with zVAD-FMK prior to treatment with etoposide significantly diminished the cleavage of Livin, in a dose-dependent manner, indicating that this is a caspase-dependent event (FIG. 3a).

The three main effector caspases are caspases 3, 6 and 7. To test whether these caspases cleave Livin in vivo, Jurkat cells were pre-incubated with specific inhibitors for either caspase 3 or 6, prior to treatment with etoposide. Caspase 3 but not caspase 6 inhibitor was able to diminish the cleavage (data not shown).

A specific inhibitor of caspase 7 has not yet been described. Thus, the MCF-7 cell line, a breast cancer cell line that lacks caspase 3 but expresses caspase 7 was used. Since endogenous Livin was not detected in MCF-7 cells, these were transfected with both Livin isoforms,. Upon induction of apoptosis using staurosporine, a clear cleavage of both isoforms, associated with a decline in the full-length protein, was observed (FIG. 3b), demonstrating that other caspases, aside from caspase 3 are able to cleave Livin in vivo.

Example 3

Effector but Not Initiator Caspases Cleave Livin In Vitro

The above results demonstrate for the first time that Livin α and β can be cleaved following the induction of apoptosis. To investigate directly which caspases are able to cleave Livin, recombinant Livin was generated in bacteria. Purified Livin α and β were incubated with either one of the recombinant active effector caspases 3, 6 and 7 or with the initiator caspases 8 and 9. As shown in FIG. 4a, effector caspases 3, 7, and relatively high concentrations of caspase 6, but not the initiator caspases 8 and 9, cleaved Livin β. The most efficient cleavage was observed when caspase 7 was used, resulting in the complete cleavage of the recombinant Livin β (FIG. 4a). Similar results were obtained when recombinant Livin α was used (data not shown). It is important to note that the difference in the amount of units results from a different definition of caspases 3 and 8 units versus caspases 6, 7 and 9 units, as discussed in the Experimental Procedures. In FIG. 4a, similar activities of caspases 3 and 7 were achieved using an appropriate colorimetric substrate. In contrast to the marked efficiency of caspase 7, caspase 6 was not able to cleave Livin at low concentrations (FIG. 4b). Treatment of recombinant Livin α and β with caspase 8 had no effect even when 90 units of this enzyme were used, while incubation with high concentrations of caspase 9 resulted in a weak cleavage, suggesting that caspase 9 might cleave Livin with a very low affinity. Incubation of Livin α and β with Granzyme B, a caspase-like protease with a broad spectrum of substrates, including effector caspase 3, did not produce any detectable cleavage fragment (data not shown).

Example 4

Mapping the Cleavage Site

The observed molecular weight of the cleaved fragments suggests that the Livin cleavage site resides somewhere near the amino-terminal or at the carboxy-terminal of the protein, after the 18 amino acids which distinguish between α and β isoforms. Amino acid sequence analysis for candidate tetrapeptides that can be potential caspase substrates at both regions, revealed the presence of two possible sites: DHVD52G at the N-terminal, and GARD238V at the C-terminal (FIG. 5a). The sequence located around aspartic acid 52 showed a high degree of similarity with the consensus substrate sequence for caspases 3 and 7 [Stennicke, H. R. et al. (2000) id ibid.; Thornberry, N. A. et al. (1997) J. Biol. Chem., 272: 17907-17911]. Constructs of both Livin isoforms were then prepared, in which either aspartic acid-52 or aspartic acid-238 was replaced by glutamic acid, termed Livin D52E and Livin D238E, respectively. Livin constructs carrying these mutations and the wild type sequence were translated in vitro and incubated with purified active caspases. Both mutant fragments Livin D238E α and β underwent cleavage similar to the wild-type protein by caspase 3 and 7, whereas mutant fragments Livin D52E α and β were not cleaved under these conditions (FIG. 5b). Although caspase 6 was able to cleave recombinant Livin produced in bacteria at relatively high concentration, it did not cleave any of the Livin isoforms that were translated in eukaryotic in vitro system.

Example 5

Livin Cleavage Produces a Pro-Apoptotic Subunit 721.221 cells can be easily transfected with various constructs [Mandelboim O. et al. (1996) id ibid]. The functional relevance of Livin cleavage was therefore tested by generating 721.221 cells stably transfected with either full-length Livin α, full-length Livin β, or the C-terminal cleavage subunits, which were cloned in pIRES-EGFP plasmid. The inventors' previous work showed that Livin α is able to protect from apoptosis induced by anti-CD95/Fas antibody in Jurkat cells [Ashhab, Y. et al. (2001) id ibid]. Similarly, 721.221 cells expressing Livin α showed a lower rate of apoptosis, following anti-CD95/Fas treatment, as compared with wild type 721.221 cells (FIG. 6a). Surprisingly, following anti-CD95/Fas treatment, cells expressing p30-Livin α showed a much higher rate of apoptosis in comparison with wild type 721.221 cells (FIG. 6a). This result indicated, unexpectedly, that the cleavage of Livin not only eliminates its anti-apoptotic activity, but also produces a subunit with a marked pro-apoptotic effect. The existence of the proteins in the transfected cells was verified by Western blot analysis (FIG. 6b).

Example 6 p28-Livin β is a More Potent Pro-Apoptotic Agent than p30-Livin α

Two attempts to generate 721.221 cells that stably express p28-Livin β did not produce stable clones, although Green Fluorescent Protein (GFP)-positive cells appeared early during the course of G418 selection. A possible explanation might be a strong pro-apoptotic activity of this subunit that lead to an early death of the 721.221 cells. Transient transfection was therefore used to assay for p28-Livin β function and to further confirm the above results. pIRES-EGFP plasmids containing either full-length Livin α, full-length Livin β, p30-Livin α, p28-Livin β, or no insert were transiently transfected into 293T cells. Cells were harvested 24 hours post-transfection. Apoptosis was determined by Annexin V/PI staining using flow cytometry, in order to analyze only GFP-positive cells. A significantly higher rate of spontaneous apoptosis was seen in the cells transfected with either p30-Livin α or p28-Livin β, in comparison to cells transfected with the full-length proteins or an empty vector (FIG. 6c). In addition, while a marked increase in GFP-positive cells was observed in cells transfected with the full-length cDNAs or the empty vector, cells transfected with cDNAs encoding the subunits showed a much lower rate of GFP-positive cells. The presence of the proteins in the transfected cells was verified by Western blot analysis (FIG. 6d).

Similar experiments were performed in LB33 Mel A1 cells, which do not express endogenous Livin, were transiently transfected with either full length Livin α, Livin β or their cleavage fragments: p30-Livin α and p28-Livin β, respectively, and empty vector as control. At the indicated times post transfection cells were analyzed for GFP percent as a marker of transfection, and the GFP-positive population was further analyzed for cell death using PI stain. Consistent with the above-shown results, transient transfection of both p30-Livin α and p28-Livin β is sufficient to induce apoptosis, in comparison to transfection with the full-length counterparts or control. However, p28-Livin β showed a much higher rate of apoptosis than p30-Livin α, at all of the time points that were tested (data not shown).

Example 7

Resistance to Chemotherapy is in Direct Correlation with Livin Expression in Primary Culture Melanoma Cells The strong expression of Livin in melanoma cell lines, and its ability to protect them from chemotherapy [Vucic, D. et al. (2000) id ibid; Ashhab, Y. (2001) id ibid] prompted the inventors to further explore the clinical significance of Livin expression and its cleavage in melanoma. Several melanoma cell lines were initially examined for the expression of Livin, XIAP and Survivin. Cell lines termed 1259-mel, 1074-mel, 1106-mel and 1612-mel were derived from patients after treatment, and showed a uniform expression of Livin, XIAP and Survivin (FIG. 7a).

LB33 A1 and B1 are two metastatic melanoma cell lines derived from the same patient before and after vaccination with autologous melanoma cells [Ikeda, H. et al. (1997) Immunity 6: 199-208; Lehmann, F. et al. (1995) Eur. J. Immunol. 25: 340-347]. The primary cell line Mel A1 expressed the HLA class I molecules: A24, A28, B13, B44, Cw6, Cw7. The patient was vaccinated repeatedly with autologous melanoma cells and achieved remission. Four years later the patient relapsed, and another cell line was generated, designated Mel B1. These cells showed no expression of the original HIA class I molecules except from A24. Strikingly, the expression of Livin was detected only in Mel B1 and not in Mel A1, while both cell lines expressed XIAP and Survivin (FIG. 7a). Furthermore, Mel B1 cells expressing high levels of Livin were completely resistant to etoposide, while Mel A1 rapidly underwent apoptosis, as determined by nuclear morphology (FIG. 7b). To further confirm these results, cells were harvested following treatment at 0, 12, 24 and 48 hours, total protein was normalized and Western blot analysis was performed, using anti-Livin antibody. Consistent with the previous results, marked Livin cleavage was not detected in Mel B1, likely due to very low rate of apoptosis (FIG. 7c, upper panel). The same Western blot membrane was stripped and exposed to anti-PARP antibody. PARP was detected in all samples, confirming similar protein content. Notably, a marked cleavage of PARP, a marker of apoptosis, was only detected in Mel A1 (FIG. 7c, lower panel).

Primary cultures of 27 melanoma patients were next analyzed for Livin, XIAP and Survivin expression. The protein content of whole cell extracts was normalized by Bradford assay, and Western blot analysis was performed. XIAP and Survivin were detected in practically all tested samples. In contrast, Livin protein was detected in 10 out of the 27 samples. Among the samples positive for Livin, a marked difference in its expression levels was observed. In FIG. 8a, representing a panel of 19 patients, melanoma samples 55182, 5556 and 55112 showed relatively high levels of both Livin isoforms, while others such as 5524 expressed only moderate levels. In contrast, a more uniform expression of XIAP and Survivin was found, with the exception of XIAP expression in ample 55207.

In order to determine whether Livin expression renders the melanoma cells resistant to chemotherapy, six melanoma samples were selected, according to their Livin expression. Samples 5556 and 55112, expressing high levels, samples 5524 and 55164, expressing intermediate levels, and samples 5530 and 5533, where no expression of Livin was observed (FIG. 8a). Cells were plated in 6-well plates 24 hours prior to exposure to etoposide (15 µg/ml). After 24 and 48 hours, cells were harvested and the percent of apoptosis determined in each sample by nuclear morphology (FIG. 8b). Remarkably, a direct correlation was observed between the rate of apoptosis and Livin expression level. Samples 5556 and 55112, with high Livin expression, were completely resistant to etoposide at the indicated concentrations and times, while moderate resistance (15-25%) was observed in samples 5524 and 55164. Finally, melanoma samples 5533 and 5530 showed a marked apoptosis rate, reaching up to 55%. Interestingly, XIAP and Survivin expression did not correlate with resistance to etoposide.

In order to demonstrate the relevance of Livin cleavage in primary melanoma, three samples: 55112 and 5524, expressing high and moderate levels of Livin respectively, and 5530, with no detectable Livin, were lysed, normalized for total protein, and analyzed by Western blot analysis (FIG. 8c). As was observed in the above experiments, the cleavage of Livin was in correlation with the apoptosis rate. Sample 55112, which was completely resistant to etoposide, showed no cleavage of Livin, sample 5524 showed moderate cleavage, appearing only 48 hours after treatment, and no Livin was detected in the melanoma sample 5530 (FIG. 8c).

The clinical data regarding these 27 patients revealed that 15 patients received chemotherapy either as the only treatment or prior to vaccination. Seven patients had disease progression while on chemotherapy, 5 of which had intermediate (5574, 5524) or high expression (55182, 55112, 5556) of Livin. Among the eight chemo-responsive patients, one patient had low level of Livin (5584), while the other seven had no Livin expression (p=0.02, Fischer exact test). Seventeen patients died, eight of which had intermediate to high levels of Livin (median survival 22.5±16 months). One patient is alive with disease. Among the nine patients with no evidence of disease (median time of follow-up 36±21 months), seven were Livin negative. Though the number of patients studied is relatively small, the correlation between Livin expression and response to chemotherapy is statistically significant. Further research will clarify the role of Livin, and its interactions with other apoptosis regulators, in the chemoresistance phenotype of melanoma.

The invention claimed is:

1. An isolated or synthetic livin-derived peptide selected from one of p30-Livin α and p28-Livin β, wherein said p30-Livin α peptide comprises the sequence as defined in SEQ ID NO:1 having pro-apoptotic activity, and wherein said p28-Livin β peptide comprises the sequence as defined in SEQ ID NO:2 having pro-apoptotic activity.

2. An isolated or synthetic peptide as defined in claim 1, wherein said p30-Livin α is denoted by the amino acid sequence as defined in SEQ ID NO:1 and said p28-Livin β is denoted by the amino acid sequence as defined in SEQ ID NO:2.

3. A composition comprising as active ingredient at least one peptide as defined in claim 1 and a pharmaceutically-acceptable carrier.

4. A composition as defined in claim 3, for inducing and/or enhancing apoptosis.

5. A composition as defined in claim 4, wherein said apoptosis is induced by a treatment or agent selected from the group consisting of etoposide, anti-CD95/Fas, TNFα and staurosporine.

6. A composition as defined in claim 4, for inducing apoptosis in malignant cells.

7. A plasmid comprising DNA encoding a p30-Livin α peptide as defined by SEQ ID NO: 1 or a p28-Livin β peptide as defined by SEQ ID NO: 2.

8. A viral vector comprising DNA encoding a p30-Livin α peptide as defined by SEQ ID NO: 1 or a p28-Livin β peptide as defined by SEQ ID NO: 2.

9. An isolated or recombinantly-produced livin fragment, said livin fragment selected from one of p30-Livin α and p28-Livin β, said fragment having pro-apoptotic activity.

10. A composition comprising as active ingredient at least one livin as defined in claim 9 and a pharmaceutically-acceptable carrier.

* * * * *

```
                        SEQUENCE LISTING

<160> NUMBER OF SEQ ID NOS: 11

<210> SEQ ID NO 1
<211> LENGTH: 246
<212> TYPE: PRT
<213> ORGANISM: Homo sapiens

<400> SEQUENCE: 1

Gly Gln Ile Leu Gly Gln Leu Arg Pro Leu Thr Glu Glu Glu Glu
1               5                   10                  15

Glu Gly Ala Gly Ala Thr Leu Ser Arg Gly Pro Ala Phe Pro Gly Met
            20                  25                  30

Gly Ser Glu Glu Leu Arg Leu Ala Ser Phe Tyr Asp Trp Pro Leu Thr
        35                  40                  45

Ala Glu Val Pro Pro Glu Leu Leu Ala Ala Gly Phe Phe His Thr
    50                  55                  60

Gly His Gln Asp Lys Val Arg Cys Phe Phe Cys Tyr Gly Gly Leu Gln
65                  70                  75                  80

Ser Trp Lys Arg Gly Asp Asp Pro Trp Thr Glu His Ala Lys Trp Phe
                85                  90                  95

Pro Ser Cys Gln Phe Leu Leu Arg Ser Lys Gly Arg Asp Phe Val His
            100                 105                 110

Ser Val Gln Glu Thr His Ser Gln Leu Leu Gly Ser Trp Asp Pro Trp
        115                 120                 125

Glu Glu Pro Glu Asp Ala Ala Pro Val Ala Pro Ser Val Pro Ala Ser
    130                 135                 140

Gly Tyr Pro Glu Leu Pro Thr Pro Arg Arg Glu Val Gln Ser Glu Ser
145                 150                 155                 160

Ala Gln Glu Pro Gly Gly Val Ser Pro Ala Glu Ala Gln Arg Ala Trp
                165                 170                 175

Trp Val Leu Glu Pro Pro Gly Ala Arg Asp Val Glu Ala Gln Leu Arg
            180                 185                 190

Arg Leu Gln Glu Glu Arg Thr Cys Lys Val Cys Leu Asp Arg Ala Val
        195                 200                 205

Ser Ile Val Phe Val Pro Cys Gly His Leu Val Cys Ala Glu Cys Ala
    210                 215                 220

Pro Gly Leu Gln Leu Cys Pro Ile Cys Arg Ala Pro Val Arg Ser Arg
225                 230                 235                 240

Val Arg Thr Phe Leu Ser
                245
```

<210> SEQ ID NO 2
<211> LENGTH: 228
<212> TYPE: PRT
<213> ORGANISM: Homo sapiens

<400> SEQUENCE: 2

Gly Gln Ile Leu Gly Gln Leu Arg Pro Leu Thr Glu Glu Glu Glu Glu
1               5                   10                  15

Glu Gly Ala Gly Ala Thr Leu Ser Arg Gly Pro Ala Phe Pro Gly Met
            20                  25                  30

Gly Ser Glu Glu Leu Arg Leu Ala Ser Phe Tyr Asp Trp Pro Leu Thr
        35                  40                  45

Ala Glu Val Pro Pro Glu Leu Leu Ala Ala Gly Phe Phe His Thr
    50                  55                  60

Gly His Gln Asp Lys Val Arg Cys Phe Phe Cys Tyr Gly Gly Leu Gln
65                  70                  75                  80

Ser Trp Lys Arg Gly Asp Asp Pro Trp Thr Glu His Ala Lys Trp Phe
                85                  90                  95

Pro Ser Cys Gln Phe Leu Leu Arg Ser Lys Gly Arg Asp Phe Val His
            100                 105                 110

Ser Val Gln Glu Thr His Ser Gln Leu Leu Gly Ser Trp Asp Pro Trp
        115                 120                 125

Glu Glu Pro Glu Asp Ala Ala Pro Val Ala Pro Ser Val Pro Ala Ser
    130                 135                 140

Gly Tyr Pro Glu Leu Pro Thr Pro Arg Arg Glu Val Gln Ser Glu Ser
145                 150                 155                 160

Ala Gln Glu Pro Gly Ala Arg Asp Val Glu Ala Gln Leu Arg Arg Leu
                165                 170                 175

Gln Glu Glu Arg Thr Cys Lys Val Cys Leu Asp Arg Ala Val Ser Ile
            180                 185                 190

Val Phe Val Pro Cys Gly His Leu Val Cys Ala Glu Cys Ala Pro Gly
        195                 200                 205

Leu Gln Leu Cys Pro Ile Cys Arg Ala Pro Val Arg Ser Arg Val Arg
    210                 215                 220

Thr Phe Leu Ser
225

<210> SEQ ID NO 3
<211> LENGTH: 298
<212> TYPE: PRT
<213> ORGANISM: Homo sapiens

<400> SEQUENCE: 3

Met Gly Pro Lys Asp Ser Ala Lys Cys Leu His Arg Gly Pro Gln Pro
1               5                   10                  15

Ser His Trp Ala Ala Gly Asp Gly Pro Thr Gln Glu Arg Cys Gly Pro
            20                  25                  30

Arg Ser Leu Gly Ser Pro Val Leu Gly Leu Asp Thr Cys Arg Ala Trp
        35                  40                  45

Asp His Val Asp Gly Gln Ile Leu Gly Gln Leu Arg Pro Leu Thr Glu
    50                  55                  60

Glu Glu Glu Glu Glu Gly Ala Gly Ala Thr Leu Ser Arg Gly Pro Ala
65                  70                  75                  80

Phe Pro Gly Met Gly Ser Glu Glu Leu Arg Leu Ala Ser Phe Tyr Asp
                85                  90                  95

```
Trp Pro Leu Thr Ala Glu Val Pro Pro Glu Leu Leu Ala Ala Ala Gly
            100                 105                 110

Phe Phe His Thr Gly His Gln Asp Lys Val Arg Cys Phe Phe Cys Tyr
            115                 120                 125

Gly Gly Leu Gln Ser Trp Lys Arg Gly Asp Asp Pro Trp Thr Glu His
            130                 135                 140

Ala Lys Trp Phe Pro Ser Cys Gln Phe Leu Leu Arg Ser Lys Gly Arg
145                 150                 155                 160

Asp Phe Val His Ser Val Gln Glu Thr His Ser Gln Leu Leu Gly Ser
                165                 170                 175

Trp Asp Pro Trp Glu Glu Pro Glu Asp Ala Ala Pro Val Ala Pro Ser
            180                 185                 190

Val Pro Ala Ser Gly Tyr Pro Glu Leu Pro Thr Pro Arg Arg Glu Val
            195                 200                 205

Gln Ser Glu Ser Ala Gln Glu Pro Gly Gly Val Ser Pro Ala Glu Ala
            210                 215                 220

Gln Arg Ala Trp Trp Val Leu Glu Pro Pro Gly Ala Arg Asp Val Glu
225                 230                 235                 240

Ala Gln Leu Arg Arg Leu Gln Glu Glu Arg Thr Cys Lys Val Cys Leu
                245                 250                 255

Asp Arg Ala Val Ser Ile Val Phe Val Pro Cys Gly His Leu Val Cys
            260                 265                 270

Ala Glu Cys Ala Pro Gly Leu Gln Leu Cys Pro Ile Cys Arg Ala Pro
            275                 280                 285

Val Arg Ser Arg Val Arg Thr Phe Leu Ser
            290                 295

<210> SEQ ID NO 4
<211> LENGTH: 280
<212> TYPE: PRT
<213> ORGANISM: Homo sapiens

<400> SEQUENCE: 4

Met Gly Pro Lys Asp Ser Ala Lys Cys Leu His Arg Gly Pro Gln Pro
1               5                   10                  15

Ser His Trp Ala Ala Gly Asp Gly Pro Thr Gln Glu Arg Cys Gly Pro
            20                  25                  30

Arg Ser Leu Gly Ser Pro Val Leu Gly Leu Asp Thr Cys Arg Ala Trp
            35                  40                  45

Asp His Val Asp Gly Gln Ile Leu Gly Gln Leu Arg Pro Leu Thr Glu
        50                  55                  60

Glu Glu Glu Glu Glu Gly Ala Gly Ala Thr Leu Ser Arg Gly Pro Ala
65                  70                  75                  80

Phe Pro Gly Met Gly Ser Glu Glu Leu Arg Leu Ala Ser Phe Tyr Asp
                85                  90                  95

Trp Pro Leu Thr Ala Glu Val Pro Pro Glu Leu Leu Ala Ala Ala Gly
            100                 105                 110

Phe Phe His Thr Gly His Gln Asp Lys Val Arg Cys Phe Phe Cys Tyr
            115                 120                 125

Gly Gly Leu Gln Ser Trp Lys Arg Gly Asp Asp Pro Trp Thr Glu His
            130                 135                 140

Ala Lys Trp Phe Pro Ser Cys Gln Phe Leu Leu Arg Ser Lys Gly Arg
145                 150                 155                 160

Asp Phe Val His Ser Val Gln Glu Thr His Ser Gln Leu Leu Gly Ser
                165                 170                 175
```

```
Trp Asp Pro Trp Glu Glu Pro Glu Asp Ala Ala Pro Val Ala Pro Ser
            180                 185                 190

Val Pro Ala Ser Gly Tyr Pro Glu Leu Pro Thr Pro Arg Arg Glu Val
        195                 200                 205

Gln Ser Glu Ser Ala Gln Glu Pro Gly Ala Arg Asp Val Glu Ala Gln
        210                 215                 220

Leu Arg Arg Leu Gln Glu Glu Arg Thr Cys Lys Val Cys Leu Asp Arg
225                 230                 235                 240

Ala Val Ser Ile Val Phe Val Pro Cys Gly His Leu Val Cys Ala Glu
                245                 250                 255

Cys Ala Pro Gly Leu Gln Leu Cys Pro Ile Cys Arg Ala Pro Val Arg
            260                 265                 270

Ser Arg Val Arg Thr Phe Leu Ser
        275                 280

<210> SEQ ID NO 5
<211> LENGTH: 27
<212> TYPE: DNA
<213> ORGANISM: Artificial Sequence
<220> FEATURE:
<223> OTHER INFORMATION: Primer for site-directed mutagenesis

<400> SEQUENCE: 5 gggaattct ggtcagagcc agtgttc                                          27

<210> SEQ ID NO 6
<211> LENGTH: 24
<212> TYPE: DNA
<213> ORGANISM: Artificial Sequence
<220> FEATURE:
<223> OTHER INFORMATION: Primer for site-directed mutagenesis

<400> SEQUENCE: 6
gggggatccg gagcccactc tgca                                            24

<210> SEQ ID NO 7
<211> LENGTH: 18
<212> TYPE: DNA
<213> ORGANISM: Artificial Sequence;
<220> FEATURE:
<223> OTHER INFORMATION: Mega-primer to introduce mutation D52E

<400> SEQUENCE: 7
cgtggaaggg cagatcct                                                   18

<210> SEQ ID NO 8
<211> LENGTH: 19
<212> TYPE: DNA
<213> ORGANISM: Artificial Sequence
<220> FEATURE:
<223> OTHER INFORMATION: Mega-primer to introduce mutation D238E

<400> SEQUENCE: 8
ccagggaagt agaggcgca                                                  19

<210> SEQ ID NO 9
<211> LENGTH: 41
<212> TYPE: DNA
<213> ORGANISM: Artificial Sequence
<220> FEATURE:
<223> OTHER INFORMATION: Primer to construct cleavage fragment
```

-continued

```
<400> SEQUENCE: 9
ggggaattca gtgttccctc catggggcag atcctgggcc a                          41

<210> SEQ ID NO 10
<211> LENGTH: 26
<212> TYPE: DNA
<213> ORGANISM: Artificial Sequence
<220> FEATURE:
<223> OTHER INFORMATION: Livin-Exp-F

<400> SEQUENCE: 10
tgttggatcc atgggaccta aagaca                                           26

<210> SEQ ID NO 11
<211> LENGTH: 27
<212> TYPE: DNA
<213> ORGANISM: Artificial Sequence
<220> FEATURE:
<223> OTHER INFORMATION: Livin-Exp-R

<400> SEQUENCE: 11
ggcaaagctt ctaggacagg aaggtgc                                          27
```